US012690749B2

(12) United States Patent
Takayama et al.

(10) Patent No.: US 12,690,749 B2
(45) Date of Patent: Jul. 28, 2026

(54) MEDICAL DEVICE OPERATION TRAINING APPARATUS

(71) Applicants: KOTOBUKI Medical Inc., Yashio (JP); National Cancer Center, Tokyo (JP)

(72) Inventors: Seiichiro Takayama, Yashio (JP); Tomonori Yano, Tokyo (JP); Yusuke Yoda, Tokyo (JP); Hironori Sunakawa, Tokyo (JP); Tomohiro Mitsui, Tokyo (JP)

(73) Assignees: KOTOBUKI Medical Inc., Yashio (JP); National Cancer Center, Tokyo (JP)

( * ) Notice: Subject to any disclaimer, the term of this patent is extended or adjusted under 35 U.S.C. 154(b) by 898 days.

(21) Appl. No.: 17/995,012

(22) PCT Filed: Nov. 12, 2021

(86) PCT No.: PCT/JP2021/041738
§ 371 (c)(1),
(2) Date: Sep. 29, 2022

(87) PCT Pub. No.: WO2022/153656
PCT Pub. Date: Jul. 21, 2022

(65) Prior Publication Data
US 2023/0210350 A1      Jul. 6, 2023

(30) Foreign Application Priority Data

Jan. 18, 2021      (JP) ................................. 2021-005642

(51) Int. Cl.
*A61B 1/00*          (2006.01)
*A61B 8/12*          (2006.01)

(52) U.S. Cl.
CPC ............ *A61B 1/00057* (2013.01); *A61B 8/12* (2013.01)

(58) Field of Classification Search
CPC ....... A61B 1/00057; A61B 8/12; A61B 1/273; A61B 1/3137; G09B 23/285
See application file for complete search history.

(56) References Cited

U.S. PATENT DOCUMENTS 6,780,016 B1      8/2004 Toly
9,257,055 B2 *   2/2016 Endo .................... G09B 23/285
(Continued)

FOREIGN PATENT DOCUMENTS

CN      104700698 A      6/2015
CN      104725595 A      6/2015
(Continued)

OTHER PUBLICATIONS

EndoGel User Manual (Oct. 5, 2025; https://medical.crkennedy.com.au/ts1641837883/attachments/Product/54590/SAendogel.tag.manual.pdf) (Year: 2016).*
(Continued)

*Primary Examiner* — Peter S Vasat
*Assistant Examiner* — Selwa A Alsomairy
(74) *Attorney, Agent, or Firm* — FLYNN THIEL, P.C.

(57)      ABSTRACT
A medical device operation training apparatus, used in performing training for operation of a medical device, includes: an affected-area simulated organ holding unit configured to hold a sheet-like affected-area simulated organ able to be incised or excised at least in part; and a path simulated organ holding unit configured to hold a path simulated organ for guiding the medical device to the affected-area simulated organ. With this apparatus, trainees can train for various manipulations with simple preparatory operations.

11 Claims, 19 Drawing Sheets

(56)     References Cited

U.S. PATENT DOCUMENTS

| | | | |
|---|---|---|---|
| 9,855,617 B2 | 1/2018 | Liang et al. | |
| 9,959,786 B2 | 5/2018 | Breslin et al. | |
| 10,043,416 B2 | 8/2018 | Kogiso | |
| 11,056,021 B2 | 7/2021 | Takayama | |
| 2014/0030682 A1 | 1/2014 | Thilenius | |
| 2019/0236986 A1* | 8/2019 | Velasco | G09B 9/00 |
| 2021/0201700 A1* | 7/2021 | Abe | G09B 23/32 |
| 2021/0272478 A1* | 9/2021 | Shimoda | G09B 23/285 |

FOREIGN PATENT DOCUMENTS

| | | | |
|---|---|---|---|
| CN | 109875864 A | | 6/2019 |
| CN | 112204638 A | | 1/2021 |
| JP | 2004-49479 A | | 2/2004 |
| JP | 2006-81568 A | | 3/2006 |
| JP | 3162161 U | | 8/2010 |
| JP | 2011-113056 A | | 6/2011 |
| JP | 2013-127496 A | | 6/2013 |
| JP | 2015085017 A | * | 5/2015 |
| JP | 2015-532451 A | | 11/2015 |
| JP | 2016-538138 A | | 12/2016 |
| JP | 2019-12126 A | | 1/2019 |
| JP | 2019-207304 A | | 12/2019 |
| JP | 2020-190760 A | | 11/2020 |
| WO | 2016/002411 A1 | | 1/2016 |
| WO | 2017/010190 A1 | | 1/2017 |
| WO | 2020/240884 A1 | | 12/2020 |

OTHER PUBLICATIONS

Todd H. Baron (New ex-vivo porcine model for endoscopic ultrasound-guided training in transmural puncture and drainage of pancreatic cysts and fluid collections (with videos) Mar. 2015 (Year: 2015).*

JP-2015085017-A Translation (Year: 2015).*

Office Action issued in corresponding Chinese Application No. 202180026686.X, dated Nov. 7, 2024 (6 pages).

International Search Report, with English translation, issued in corresponding International Application No. PCT/JP2021/041738, date of mailing Jan. 25, 2022 (5 pages).

Written Opinion of the International Searching Authority issued in corresponding International Application No. PCT/JP2021/041738, date of mailing Jan. 25, 2022 (3 pages).

Office Action issued in corresponding Japan Application No. 2021-005642, dated Oct. 1, 2024 (4 pages).

EngoGel User Manual (version 3.0), pp. 1-4, (Apr. 1, 2019).†

Jun et al., "Evaluation of a Balloon-Type Vaginal Endoscope Based on Three-Dimensional Printing Technology for Self-Assessment of Pelvic Organ Prolapse," pp. 1-13 (2020).†

Screen captures from YouTube video clip entitled "EndoBench Measurement Setup," 1 page, uploaded on Dec. 23, 2010 at https://www.youtube.com/watch?v=unEz1tCVog0.†

Baron et al, "New ex-vivo porcine model for endoscopic ultrasound guided training in transmural puncture and drainage of pancreatic cysts and fluid collections," pp. 34-39 (2015).†

Hirsoe et al., "Development of a new ex vivo model for evaluation of endoscopic submucosal injection materials performance," pp. 219-225 (2018).†

Excerpts from EndoToday "EndoGEL ESD Hands-on Training," 2 pages, uploaded on Jan. 3, 2020 at http://endotoday.com/endotoday02/endogel.html.†

D. Surangsrirat, "Computer Integrated Endoscopic Simulator for Training in Esophagogastroduodenoscopy," pp. 1-117 (2011).†

* cited by examiner

† cited by third party

FIG. 8

| | 0 | 10 | 20 | 30 | 40 | 50 | 60 | 70 | 80 | 90 | 100 | |
|---|---|---|---|---|---|---|---|---|---|---|---|---|
| Pedestal Planer Direction Relative Movement Mechanism — Y-Axis Direction | | 110 | 120 | 130 | 140 | 150 | 160 | 170 | 180 | 190 | 200 | |
| Pedestal Planer Direction Relative Movement Mechanism — X-Axis Direction | 20 | 10 | 0 | -10 | -20 | -30 | -40 | -50 | | | | |
| Pedestal Perpendicular Direction Relative Movement Mechanism | 0 | 10 | 20 | 30 | 40 | 50 | 60 | 70 | 80 | | | |
| Pedestal Pen-Perpendicular Axis Relative Movement Mechanism | V1 | V2 | V3 | V4 | V5 | V6 | V7 | V8 | V9 | V10 | V11 | V12 |
| Pen-Lateral Axis Relative Movement Mechanism | W1 | W2 | W3 | W4 | W5 | W6 | W7 | W8 | W9 | W10 | W11 | W12 |
| Angle Adjustment Mechanism | -20 | -10 | 0 | 10 | 20 | 30 | 40 | | | | | |
| Second Holding Unit (First Arm) | P/SET | P/1 | P/2 | P/3 | | | | | | | | |
| Fourth Holding Unit (Second Arm) | Q/SET | Q/1 | Q/2 | | | | | | | | | |
| Tension Adjustment Mechanism | Near Position | Far Position | | | | | | | | | | |
| Second-Path Simulated Organ Holding Unit | Not Used | Used | | | | | | | | | | |

MEDICAL DEVICE OPERATION TRAINING APPARATUS

TECHNICAL FIELD

The present invention relates to an apparatus for performing training for operation of a medical device such as an endoscopic surgical device.

BACKGROUND ART

In conducting procedures, such as endoscopic examination, endoscopic surgery, and the like, it has heretofore been necessary for doctors to be proficient in the operation of various medical devices, including endoscope manipulation. Moreover, surgical assistance robots for performing laparoscopic surgery using robot arms (robot forceps) have become prevalent in recent years, and doctors need to master the techniques for operating the surgical assistance robots.

For example, a training apparatus for practicing endoscope manipulation, including a stationary table to which a pseud trunk is fixed so as to be rotatable about a horizontal axis has been proposed (see Japanese Patent Application Laid-Open No. 2004-49479). The pseudo trunk includes simulated organs located therein. A trainee changes the fixing angle of the pseudo trunk to reproduce a patient's lateral position and supine position, and the trainee inserts an endoscope into the simulated organs in the pseudo trunk to practice endoscope manipulation.

For example, an apparatus for hermetically holding both ends of a tubular organ, cut out from the living body of a non-human animal, on a fixed table has also been proposed (see Japanese Patent Application Laid-Open No. 2006-81568). By inserting an endoscope into a tubular organ that is filled and distended with air with this training apparatus, a trainee can practice endoscope manipulation with a feel similar to that in an actual clinical setting.

SUMMARY OF INVENTION

Technical Problem

However, the training apparatus disclosed in Japanese Patent Application Laid-Open No. 2004-49479 has the problem that the overall size is large and a wide training space needs to be prepared. In addition, since the trunk itself is formed of a resin or the like, training for endoscopic surgery such as tumor excision is difficult to perform.

The training apparatus disclosed in Japanese Patent Application Laid-Open No. 2006-81568 has the problem that an intact tubular organ needs to be prepared and thus practicing endoscope manipulation is difficult.

These conventional training apparatuses also have the problem that the state of operation of the endoscope is difficult for a third party, someone other than the person practicing manipulation to recognize from the outside.

In view of the aforementioned circumstances, an object of the present invention is to provide a medical device operation training apparatus that enables training for various manipulations with simple preparatory operations.

Solution to Problem

To achieve the aforementioned object, the present invention provides a medical device operation training apparatus used in performing training for operation of a medical device, the medical device operation training apparatus including: an affected-area simulated organ holding unit configured to hold a sheet-like affected-area simulated organ able to be incised or excised at least in part; and a path simulated organ holding unit configured to hold a path simulated organ for guiding the medical device to the affected-area simulated organ.

Concerning the medical device operation training apparatus described above, the affected-area simulated organ holding unit may include a tension adjustment mechanism configured to change tension acting on the affected-area simulated organ.

Concerning the medical device operation training apparatus described above, the affected-area simulated organ holding unit may include at least a first holding unit, a second holding unit, and a third holding unit each configured to hold the affected-area simulated organ. The first holding unit, the second holding unit, and the third holding unit may be disposed in an orientation to form vertices of a triangle, whereby a surgical surface including the tringle is formed at a surface of the affected-area simulated organ.

Concerning the medical device operation training apparatus described above, the affected-area simulated organ holding unit may further include a fourth holding unit configured to hold the affected-area simulated organ. The first holding unit, the second holding unit, the third holding unit, and the fourth holding unit may be disposed to surround the affected-area simulated organ in this order. A first diagonal line connecting the first holding unit and the third holding unit and a second diagonal line connecting the second holding unit and the fourth holding unit may be positioned to an orientation of skew lines.

Concerning the medical device operation training apparatus described above, the affected-area simulated organ holding unit may include a second holding unit displacement mechanism configured to displace the second holding unit in a direction including at least a circumferential direction component about a line connecting the first holding unit and the third holding unit.

Concerning the medical device operation training apparatus described above, the affected-area simulated organ holding unit may hold the affected-area simulated organ so that a surface of the affected-area simulated organ forms a curved surface of hyperboloidal shape, hyperbolic paraboloidal shape, or saddle shape.

Concerning the medical device operation training apparatus described above, the path simulated organ may include a path member including a band-like region of band shape extending in a path direction, with raised edges on both sides in a band width direction.

Concerning the medical device operation training apparatus described above, the band-like region included in the path member may be a widening region where a band width increases from upstream to downstream.

Concerning the medical device operation training apparatus described above, the band-like region of the path member may be open-topped.

Concerning the medical device operation training apparatus described above, the path member and the affected-area simulated organ may simulate a part of a stomach inner wall, and the path member and the affected-area simulated organ may move relative to each other.

Concerning the medical device operation training apparatus described above, the path simulated organ may include a cylindrical path member of cylindrical shape upstream of the path member.

Concerning the medical device operation training apparatus described above, the path member may have a maximum width greater than a width of an inner wall of the cylindrical path member.

The medical device operation training apparatus described above may include a peri-lateral axis relative movement mechanism configured to change a relative angle between the path simulated organ and the affected-area simulated organ about a lateral axis extending in a horizontal direction.

To achieve the aforementioned object, the present invention provides a medical device operation training apparatus used in performing training for operation of a medical device, the medical device operation training apparatus including an affected-area simulated organ holding unit configured to hold a sheet-like affected-area simulated organ able to be incised or excised at least in part. The affected-area simulated organ holding unit holds the affected-area simulated organ so that a surface of the affected-area simulated organ forms a curved surface of hyperboloidal shape, hyperbolic paraboloidal shape, or saddle shape.

To achieve the aforementioned object, the present invention provides a medical device operation training apparatus used in performing training for operation of a medical device, the medical device operation training apparatus including an affected-area simulated organ holding unit configured to hold a sheet-like affected-area simulated organ able to be incised or excised at least in part. The affected-area simulated organ holding unit includes at least a first holding unit, a second holding unit, a third holding unit, and a fourth holding unit each configured to hold the affected-area simulated organ. The first holding unit, the second holding unit, the third holding unit, and the fourth holding unit are disposed to surround the affected-area simulated organ in this order. A first diagonal line connecting the first holding unit and the third holding unit and a second diagonal line connecting the second holding unit and the fourth holding unit are positioned to an orientation of skew lines.

Advantageous Effects of Invention

According to the present invention, an excellent effect of providing a medical device operation training apparatus that enables training for various manipulations with simple preparatory operations can be provided.

BRIEF DESCRIPTION OF DRAWINGS

FIG. 8 is a table showing a setting sheet of the medical device operation training apparatus.

DESCRIPTION OF EMBODIMENTS

An embodiment of the present invention will be described below with reference to the accompanying drawings.

Overall Configuration

Figure 1:
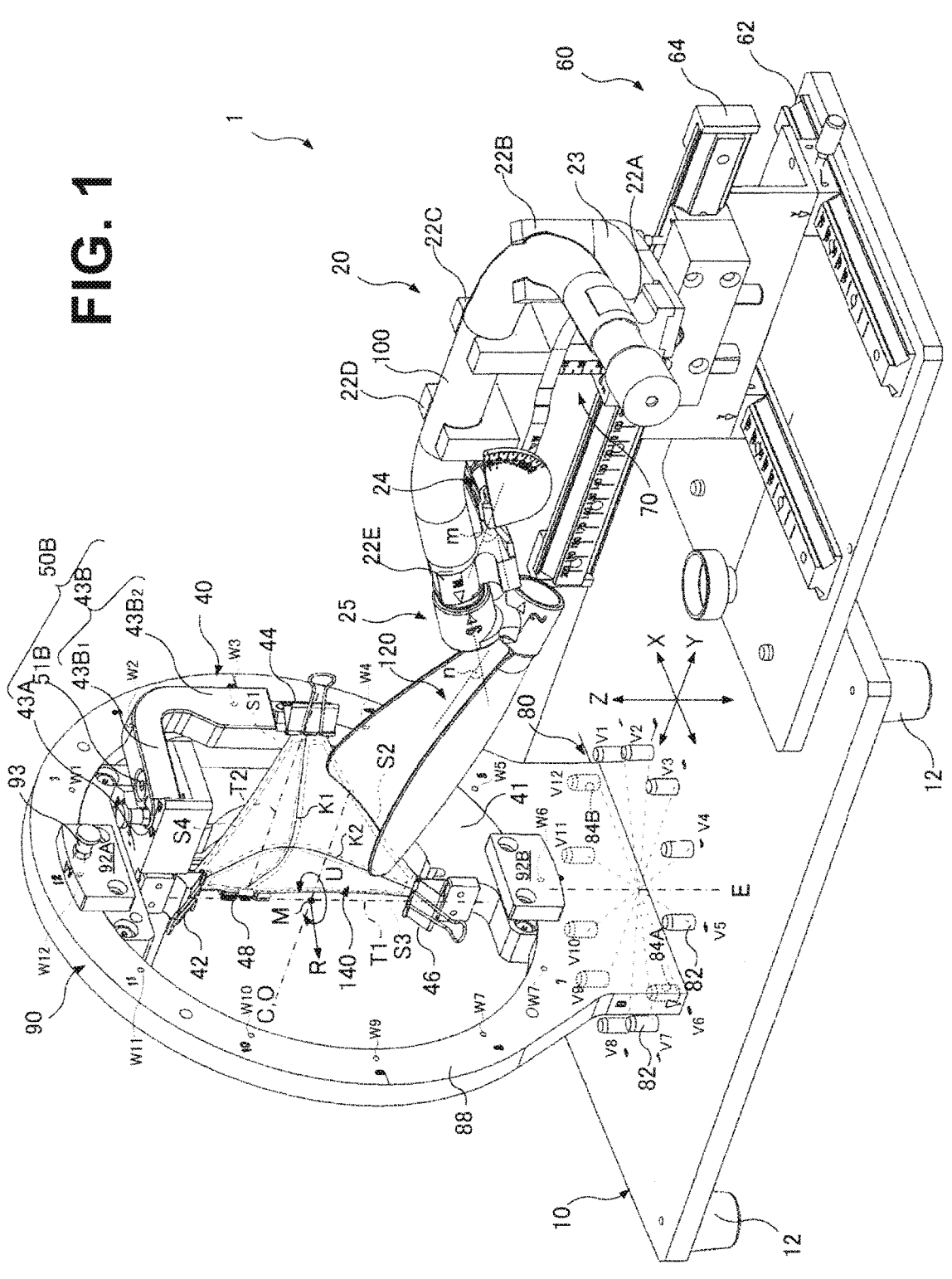
FIG. 1 is a perspective view illustrating a medical device operation training apparatus according to the present embodiment in a first curved orientation.
Figure 2:
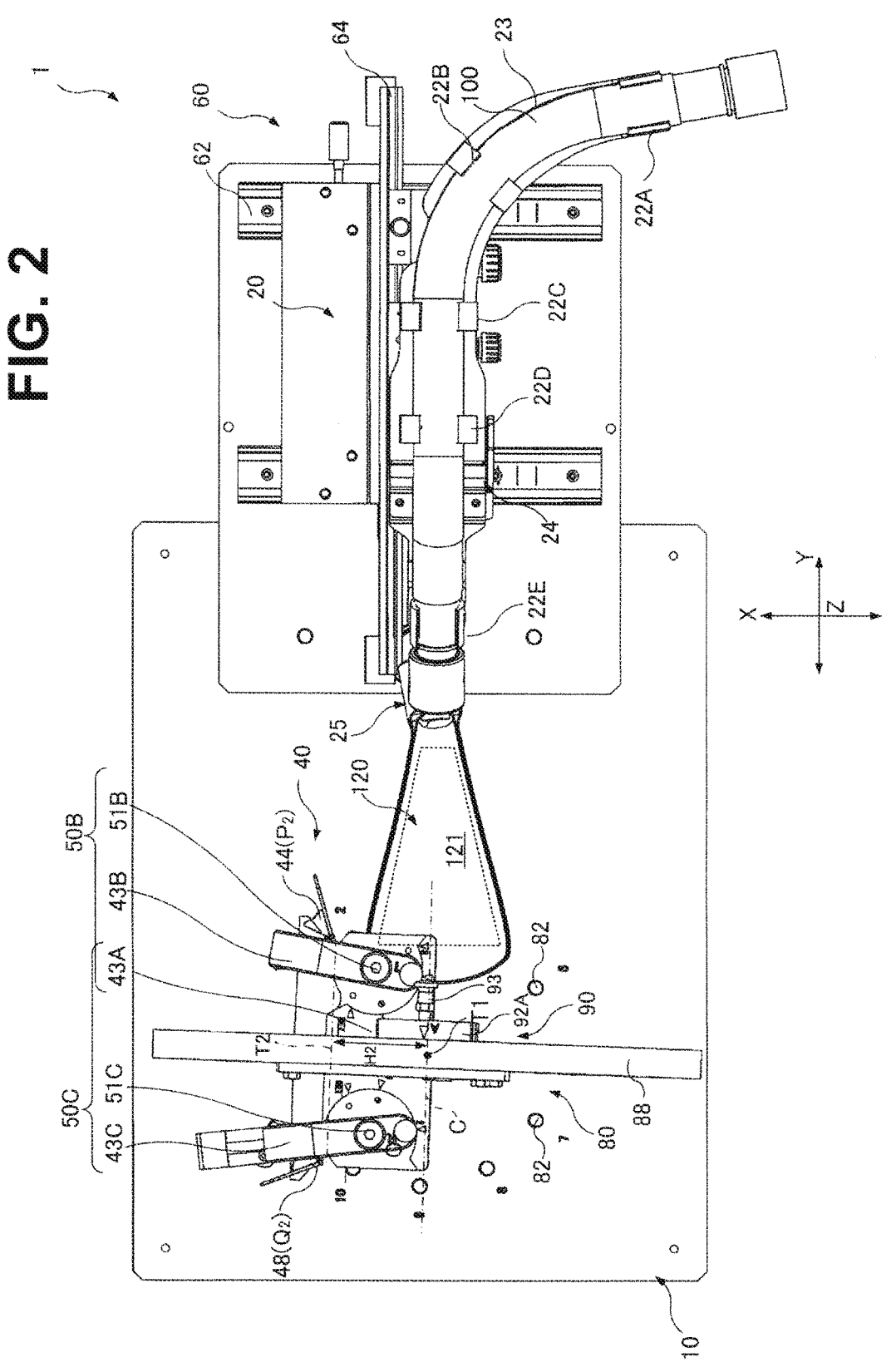
FIG. 2 is a plan view illustrating the medical device operation training apparatus in the first curved orientation.
Figure 3:
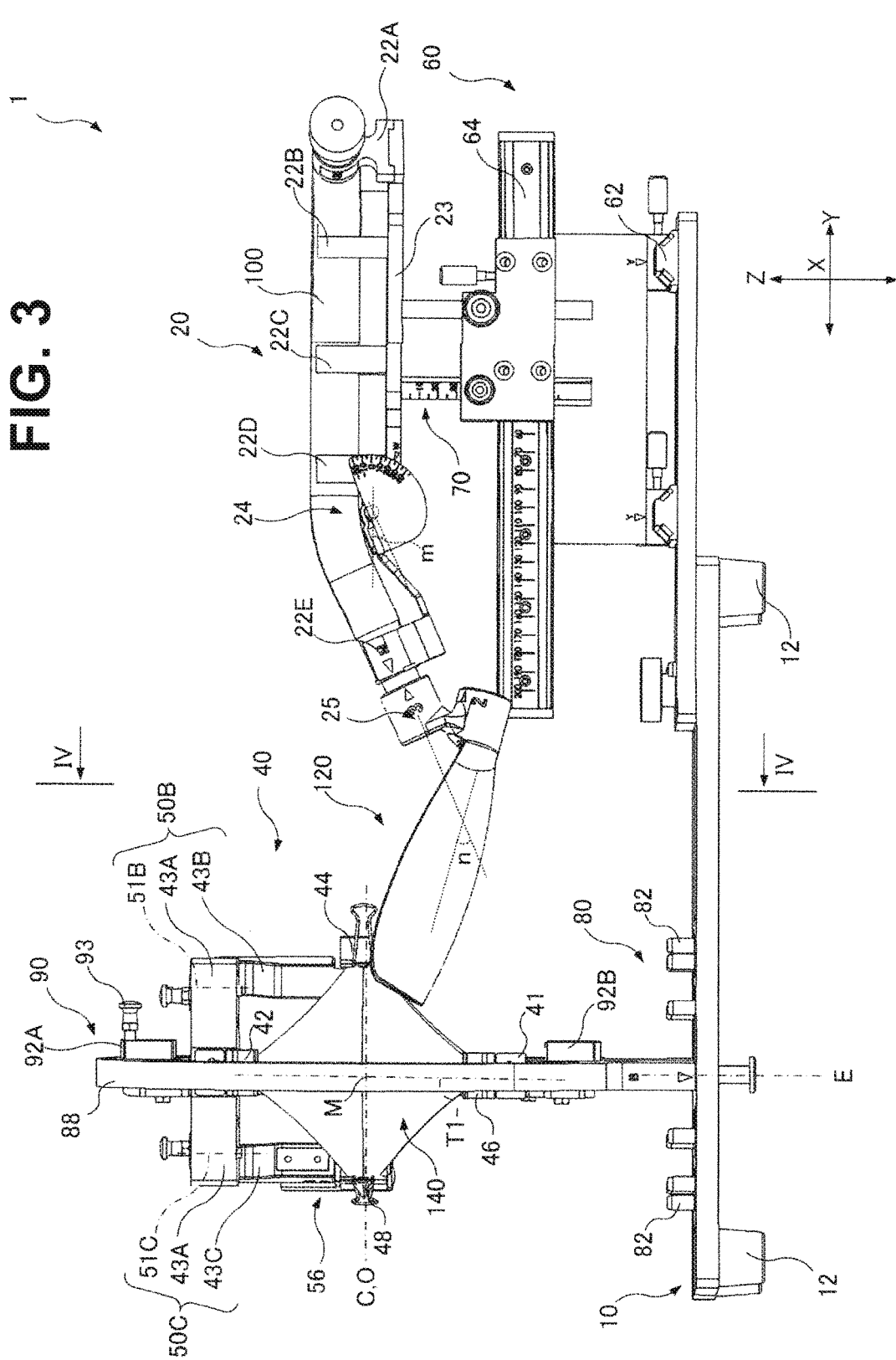
FIG. 3 is a front view illustrating the medical device operation training apparatus in the first curved orientation.

FIGS. 1 to 3 show an overall configuration of a medical device operation training apparatus (hereinafter, training apparatus) 1. Regarding this training apparatus 1, the case of practicing operation of an endoscope in an endoscopic examination or endoscopic surgery is assumed. However, the present invention is not limited thereto.

The training apparatus 1 includes a pedestal 10, a first-path simulated organ holding unit 20, a second-path simulated organ holding unit 25, an affected-area simulated organ holding unit 40, a pedestal planar direction relative movement mechanism 60, a pedestal vertical direction relative movement mechanism 70, a pedestal peri-perpendicular axis relative movement mechanism 80, and a peri-lateral axis relative movement mechanism 90.

The pedestal 10 has a plate structure with legs 12 at four corners. While the present embodiment shows an exemplary case where the surface (top surface) of the pedestal 10 is a horizontal surface, the pedestal 10 may be situated with the surface oblique to the horizontal.

For convenience of description, a desired direction parallel to the surface of the pedestal 10 will be defined as an X-axis. A direction parallel to the surface of the pedestal 10 and orthogonal to the X-axis will be defined as a Y-axis. A direction perpendicular to the surface of the pedestal 10 (X-Y plane) will be defined as a Z-axis. The X-axis may be referred to as a front-to-rear axis, the Y-axis may be referred to as a lateral axis, and the Z-axis may be referred to as a pedestal perpendicular axis. On the Y-axis (lateral axis), the side closer to the first-path simulated organ holding unit 20 may be referred to as a Y-axis operator side, and the side closer to the affected-area simulated organ holding unit 40 may be referred to as a Y-axis affected area side. On the X-axis (front-to-rear axis), the direction toward an operator may be referred to as an X-axis near side, and the direction away from the operator may be referred to as an X-axis far side.

<First-Path Simulated Organ Holding Unit>

The first-path simulated organ holding unit 20 is disposed on the pedestal 10 and holds a first-path simulated organ 100. The first-path simulated organ 100 here includes a cylindrical member (cylindrical path member) formed of a flexible resin. In the present embodiment, the first-path simulated organ 100 functions as a simulated organ simulating an oral cavity and an esophagus. While the first-path simulated organ 100 here is described to be a cylindrical member having a circular cross section as an example, the present invention is not limited thereto. The first-path simulated organ 100 can have any structure that can guide a medical device along a desired path, like a cylindrical shape having a polygonal cross section, a semicylindrical (partial cylindrical) shape, and a groove shape. The first-path simulated organ holding unit 20 desirably has a width of less than 40 mm, preferably less than 30 mm. The second-path simulated organ holding unit 25 to be described below has a maximum width of 40 mm or more, and from a comparative standpoint, the first-path simulated organ holding unit 20 can be defined as a narrow-width path member.

The first-path simulated organ holding unit 20 includes holders 22A to 22E that hold the first-path simulated organ 100 longitudinally at a plurality of points, and a base 23 on which the holders 22A to 22E are placed. The path direction of the path simulated organ 100 can be freely changed depending on the layout of the holders 22A to 22E. In the present embodiment, an upstream section of the path simulated organ 100 is held by the holder 22A to simulate a living body's oral cavity extending in the X-axis direction. The downstream side of the upstream section is held by the holder 22B to form a curved path curved in the Y-axis direction. A middle section located downstream of the curved path is held by the holders 22C and 22D to extend in the Y-axis direction, simulating a so-called esophagus. The section downstream of the middle section is held by the holder 22E to curve in the downward Z-axis direction toward the Y-axis affected area side, simulating the tilt outlet of the esophagus to the stomach.

(Angle Adjustment Mechanism)

An angle adjustment mechanism 24 having a hinge structure is provided on the base 23 of the first-path simulated organ holding unit 20. This hinge structure is able to adjust the tilt angle of the holder 22E, or more specifically, a tilt angle m at which the holder 22E makes a displacement in the downward Z-axis direction toward the Y-axis affected area side. The tilt angle varies from patient to patient, depending on the lateral position of the living body. The angle adjustment mechanism 24 enables training at various tilt angles. As shown in the setting sheet of FIG. 8, when the horizontal state is set to 0°, the angle adjustment mechanism 24 can be set to 10°, 20°, 30°, and 40° in the downward Z-axis direction (positive angle direction) and can be set to −10° and −20° in the upward Z-axis direction (negative angle direction).

<Second-Path Simulated Organ Holding Unit>

Figure 18:
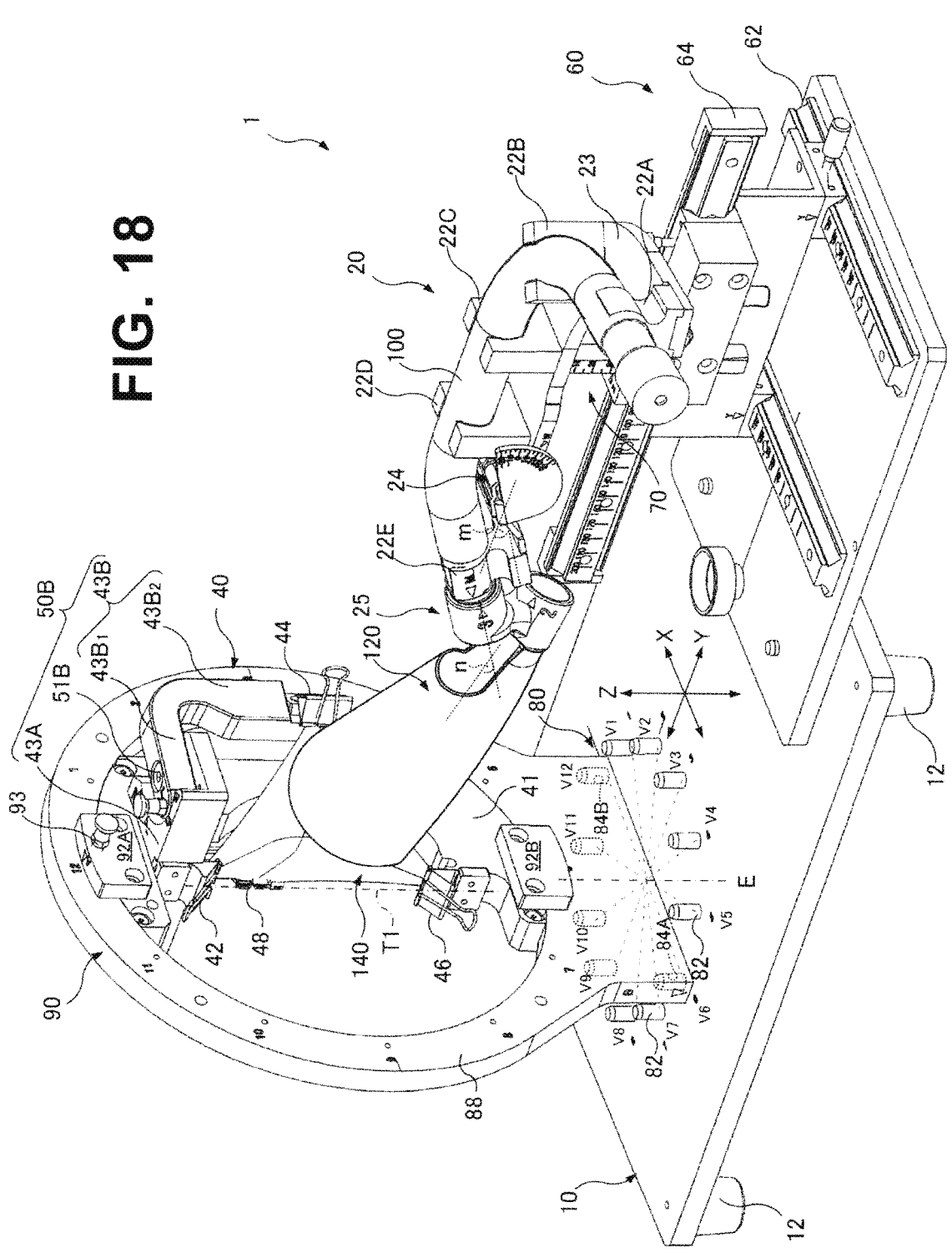
FIG. 18 is a perspective view illustrating a modification of the medical device operation training apparatus.

The second-path simulated organ holding unit 25 here is a member fixed to the bottom end of the first-path simulated organ 100, and holds a second-path simulated organ 120. The second-path simulated organ 120 is a plate-like or cylindrical path member having a desired rigidity, formed of a resin, metal, or the like, and simulates a part of a stomach wall. The second-path simulated organ 120 according to the present embodiment is a path member including a band-like region 121 (see FIG. 2) of band shape extending in the path direction, with raised edges on both sides in a band width direction. This band-like region 121 can be further defined as a widening path member since the band width increases gradually or stepwise from upstream to downstream. In the present embodiment, the band-like region 121 is open-topped. The second-path simulated organ 120 can thus be defined as an open path member of so-called partial cylindrical shape or curved spatula shape, which improves visibility from outside. However, the second-path simulated organ 120 is not limited to an open type. As illustrated in FIG. 18, the second-path simulated organ 120 may have a (widening) cylindrical structure partly including the band-like region 121 inside, like a cylindrical shape, a horn shape, or a (circular) frustrum shape. The band-like region 121 of the second-path simulated organ holding unit 25 desirably has a maximum width of, e.g., 40 mm or more, preferably 60 mm or more. This preference is due to the second-path simulated organ holding unit 25 simulating the inner wall near the inlet of the stomach and an adequate width being thus needed. As a result, the maximum width of the second-path simulated organ holding unit 25 is greater than that of the first-path simulated organ 100, which simulates the esophagus, and the second-path simulated organ holding unit 25 can be defined as a wide-width path member.

The second-path simulated organ 120 is disposed so as to be continuous with the downstream side of the bottom end (esophagus outlet) of the first-path simulated organ 100 by the second-path simulated organ holding unit 25. The path direction (extending direction) of the bottom end of the first-path simulated organ 100 and the path direction (extending direction) of the second-path simulated organ 120 are at an angle n. Although not shown in particular, the second-path simulated organ holding unit 25 may include an angle adjustment mechanism capable of adjusting the angle m. As shown in the setting sheet of FIG. 8, whether to use the second-path simulated organ holding unit and the second-path simulated organ 120 can be selected.

<Affected-Area Simulated Organ Holding Unit>

The affected-area simulated organ holding unit 40 holds an affected-area simulated organ 140 able to be incised or excised at least in part. In the present embodiment, the affected-area simulated organ 140 is formed of a flexible and/or elastic sheet member. For example, a simulated animal organ sheet described in Japanese Patent Application No. 2016-538138 can be used as the affected-area simulated organ 140. In other words, the entire description of Japanese Patent Application No. 2016-538138 (WO 2017/010190) is incorporated herein. For example, the simulated animal organ can be manufactured by a molding step of molding a gelatinized mixture of water and a raw material consisting mainly of mannans into a molded article, and a low temperature step of maintaining the molded article in a low temperature environment where the temperature is lower than normal temperature.

The affected-area simulated organ holding unit 40 includes a first holding unit 42, a second holding unit 44, a third holding unit 46, and a fourth holding unit 48. The first holding unit 42, the second holding unit 44, the third holding unit 46, and the fourth holding unit 48 hold the sheet-like affected-area simulated organ 140 in this order along the circumferential direction (peripheral direction of the sheet). The first holding unit 42, the second holding unit 44, the third holding unit 46, and the fourth holding unit 48 here are pinching members with an elastic clip structure, and pinch and hold the periphery of the affected-area simulated organ 140.

For convenience of description, a line connecting the first holding unit 42 and the third holding unit 46 will be defined as a first diagonal line T1. A line connecting the second holding unit 44 and the fourth holding unit 48 will be defined as a second diagonal line T2. A line that crosses the midpoint M of the first diagonal line T1 and is parallel to the Y-axis will be defined as a reference axis C.

The affected-area simulated organ holding unit 40 further includes a first base 41, which supports the first holding unit 42 and the third holding unit 46, and a second base 43, which supports the second holding unit 44 and the fourth holding unit 48. A tension adjustment mechanism 56 is disposed between the second base 43 and the fourth holding unit 48.

The first base 41 is a U-shaped or C-shaped member extending in parallel with the first diagonal line T1 while making a detour to avoid a region including the first diagonal line T1, which connects the first holding unit 42 and the third holding unit 46. In other words, the first base 41 supports the first holding unit 42 and the third holding unit 46 at both ends thereof while leaving a simulated organ holding space between the first holding unit 42 and the third holding unit 46. The first base 41 is able to rotate about the Y-axis by using the peri-lateral axis relative movement mechanism 90.

The second base 43 is held by the first base 41. The second base 43 is a member that is U-shaped or C-shaped in order to avoid interference with a region including the second diagonal line T2 connecting the second holding unit 44 and the fourth holding unit 48. More specifically, the second base 43 includes a seat portion 43A that is fixed to the first base 41 and extends in the Y-axis direction, a first arm 43B pivotably disposed on the Y-axis operator side of the seat portion 43A, and a second arm 43C pivotably disposed on the Y-axis affected area side of the seat portion 43A.

(Holding Unit Displacement Mechanisms)

The first arm 43B is an L-shaped member and swingably held at one end on a first pivot shaft 51B of the seat portion 43A. The second holding unit 44 is disposed on the other end of the first arm 43B. The first pivot shaft 51B is parallel to the first diagonal line T1. As illustrated in FIG. 2, the first pivot shaft 51B is offset to one side (in FIG. 2, upper side) with the reference axis C as the border when seen along the first diagonal line T1. Returning to FIG. 1, one of the sides, 43B$_1$, of the L shape of the first arm 43B is at an angle relative to the first diagonal line T1. Here, the side 43B$_1$ extends in a direction approximately perpendicular to the first diagonal line T1. The other side 43B$_2$ of the L shape of the first arm 43B extends in a direction parallel to the first diagonal direction T1. The second holding unit 44 is fixed to the far end of the side 43B$_2$ near the midpoint M of the first diagonal line T1. As shown by dotted lines in FIG. 6, when the first arm 43B is swung, the second holding unit 44 located on the Y-axis operator side of the first diagonal line T1 can thus reciprocate in directions including at least a circumferential direction component U about the first diagonal line T1 (i.e., in a state where the movement includes not only a radial direction component with respect to the first diagonal line T1). In other words, the seat portion 43A, the first pivot shaft 51B, and the first arm 43B constitute a second holding unit displacement mechanism 50B for displacing the second holding unit 44 in directions including at least the circumferential direction component U about the first diagonal line T1.

The second arm 43C is an L-shaped member and swingably held at one end on a second pivot shaft 51C of the seat portion 43A. The fourth holding unit 48 is disposed on the other end of the second arm 43C. The second pivot shaft 51C is parallel to the first diagonal line T1. As illustrated enlarged in FIG. 5, the second pivot shaft 51C is offset to one side (the same side as the first pivot shaft 51B is offset to) with the reference axis C as the border when seen along the first diagonal line T1. One of the sides, 43C$_1$, of the L shape of the second arm 43C is at an angle relative to the first diagonal line T1. Here, the side 43C$_1$ extends in a direction approximately perpendicular to the first diagonal line T1. The other side 43C$_2$ of the L shape of the second arm 43C extends in a direction parallel to the first diagonal line T1. The fourth holding unit 48 is fixed, via the tension adjustment mechanism 56, to the far end of the side 43C$_2$ near the midpoint M of the first diagonal line T1. As illustrated in FIG. 6, when the second arm 43C is swung, the fourth holding unit 48 located on the Y-axis affected area side of the first diagonal line T1 can thus reciprocate in directions including at least the circumferential direction component U about the first diagonal line T1. In other words, the seat portion 43A, the second pivot shaft 51C, and the second arm 43C constitute a fourth holding unit displacement mechanism 50C for displacing the fourth holding unit 48 in directions including the circumferential direction component U about the first diagonal line T1.

(Tension Adjustment Mechanism)

Figure 5:
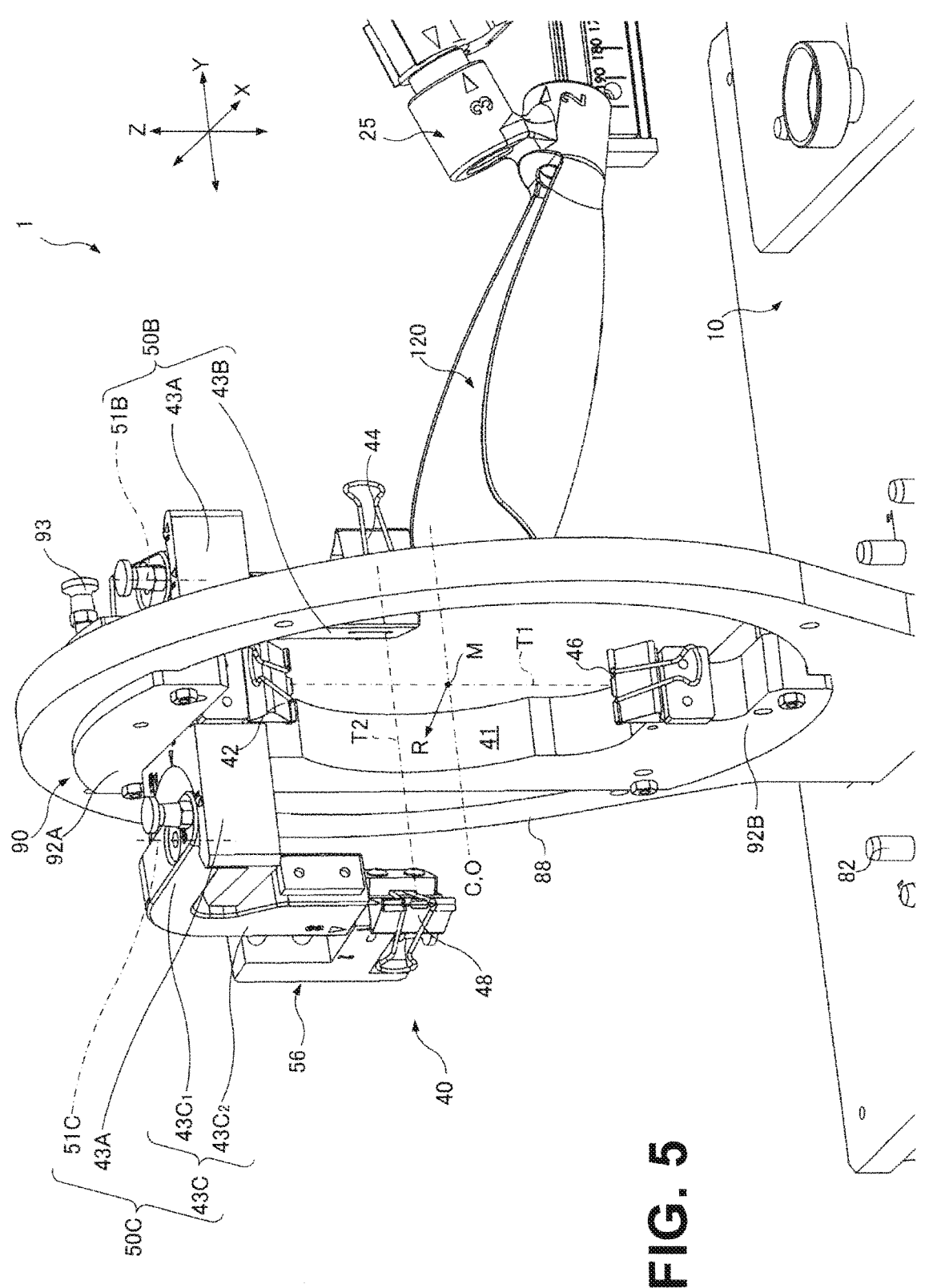
FIG. 5 is an enlarged perspective view illustrating a part of the medical device operation training apparatus in the first curved orientation.
Figure 6:
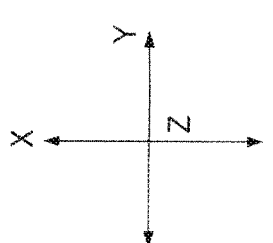
FIG. 6 is an enlarged plan view illustrating a part of the medical device operation training apparatus in the first curved orientation.

As illustrated in FIG. 5, the tension adjustment mechanism 56 is a translation mechanism for reciprocating the fourth holding unit 48 on a straight line along a direction parallel to the one side 43C$_1$ of the second arm 43C. As a result, the tension adjustment mechanism 56 plays the role of enabling the fourth holding unit 48 to reciprocate in directions including a radial direction component R with respect to the first diagonal line T1. A position close to the first diagonal line T1 will be defined as a "near position", and a position away from the first diagonal line T1 will be defined as a "far position". While the tension adjustment mechanism 56 here is described to be disposed on the fourth holding unit 48 side, the tension adjustment mechanism 56 may be disposed on the second holding unit 44 side or on both the second holding unit 44 side and the fourth holding unit 48 side. A tension adjustment mechanism may also be disposed on the first holding unit 42 and/or third holding unit 46 side(s). In such a case, the first holding unit 42 and/or the third holding unit 46 can be reciprocated in directions including at least a radial direction component with respect to the second diagonal line T2, which connects the second holding unit 44 and the fourth holding unit 48.

Note that the second holding unit displacement mechanism 50B and the fourth holding unit displacement mechanism 50C also enable the second holding unit 44 and the fourth holding unit 48 to reciprocate in directions including a radial direction component R with respect to the first diagonal line T1. In the present embodiment, the second holding unit displacement mechanism 50B and the fourth holding unit displacement mechanism 50C thus also serve as a tension adjustment mechanism.

(Description of Layout of Holding Units)

Next, the layout of the first holding unit 42, the second holding unit 44, the third holding unit 46, and the fourth holding unit 48 by the affected-area simulated organ holding unit 40 will be described. For convenience of description, when seen along the first diagonal line T1 connecting the first holding unit 42 and the third holding unit 46 in a specific direction, one side with the reference axis C as the border may be referred to as a "surgical surface one side", and the other side with the reference axis C as the border may be referred to as the "surgical surface counter side".

As illustrated in FIG. 1, three points selected from the four holding positions of the first holding unit 42, the second holding unit 44, the third holding unit 46, and the fourth holding unit 48 form the vertices of a triangle. A surgical surface is formed on the affected-area simulated organ 140 by holding the affected-area simulated organ 140 using the three points.

Such three points can be selected in various ways. For example, a first surgical surface S1 is formed with the first holding unit 42, the second holding unit 44, and the third holding unit 46 as the three holding positions. As another example, a second surgical surface S2 is formed with the second holding unit 44, the third holding unit 46, and the fourth holding unit 48 as the three holding positions. As yet another example, a third surgical surface S3 is formed with the first holding unit 42, the third holding unit 46, and the fourth holding unit 48 as the three holding positions. As yet another example, a fourth surgical surface S4 is formed with the first holding unit 42, the second holding unit 44, and the fourth holding unit 48 as the three holding positions.

In other words, the present embodiment provides the four holding positions of the first holding unit 42, the second holding unit 44, the third holding unit 46, and the fourth holding unit 48. However, the present invention is not limited thereto, and a surgical plane can be provided if there are at least three holding units at three respective points. The first to fourth surgical surfaces S1 to S4 may be curved surfaces or bent surfaces.

If the affected-area simulated organ 140 is held at four points, at least, including the first holding unit 42, the second holding unit 44, the third holding unit 46, and the fourth holding unit 48, two surgical surfaces are formed at a time, with three holding positions each. This increases the area of the surgical surfaces. Although not shown in particular, five or more holding units can be disposed to further increase the area of the surgical surfaces.

The first diagonal line T1 connecting the first holding unit 42 and the third holding unit 46 is at an angle relative to the Y-axis. Here, the first diagonal line T1 is perpendicular to the Y-axis. The second diagonal line T2 connecting the second holding unit 44 and the fourth holding unit 48 is at an angle relative to the first diagonal line T1. Here, the second diagonal line T2 is perpendicular to the first diagonal line T1.

As illustrated enlarged in FIG. 6, when seen along the first diagonal line T1 in a specific direction, the second holding unit 44 has the following four positioning points: a reference position $P_{SET}$ where the second holding unit 44 is closest to the reference axis C; a one-side first displacement position $P_1$ where the second holding unit 44 is swung to one side of the reference axis C at a first angle; a one-side second displacement position $P_2$ where the second holding unit 44 is swung and displaced to the one side of the reference axis C at a second angle (greater than the first angle); and a one-side third displacement position $P_3$ where the second holding unit 44 is swung and displaced to the one side of the reference axis C at a third angle (greater than the second angle).

The fourth holding unit 48 has the following three positioning points: a reference position $Q_{SET}$ where the fourth holding unit 48 is closest to the reference axis C; a one-side first displacement position $Q_1$ where the fourth holding unit 48 is displaced to the one side of the reference axis C at a first angle; and a one-side second displacement position $Q_2$ where the fourth holding unit 48 is swung and displaced to the one side of the reference axis C at a second angle (greater than the first angle). Such positions are reflected on the setting sheet of FIG. 8 as well.

(Description of Preparatory Orientation)

FIGS. 10 to 13 show the training apparatus 1 in a state where the second holding unit 44 is positioned to the reference position $P_{SET}$ and the fourth holding unit 48 is positioned to the reference position $Q_{SET}$, for example. The second diagonal line T2 is approximately parallel to the reference axis C, and crosses or comes very close to the first diagonal line T1. Both the first pivot shaft 51B and the second pivot shaft 51C are offset to the surgical surface one side with respect to the first diagonal line T1. The second holding unit 44 and the fourth holding unit 48 are thus brought close to the first diagonal line T1 by the pivoting of the first arm 43B and the second arm 43C. Since the affected-area simulated organ 140 does not need to be strained more than necessary in the direction of the second diagonal line T2 when installing the affected-area simulated organ 140, an orientation (preparatory orientation) results in which the affected-area simulated organ 140 can be easily pinched by the second holding unit 44 and the fourth holding unit 48. For convenience of description, the affected-area simulated organ 140 is omitted in FIGS. 12 and 13. The second-path simulated organ 120 is omitted in the cross section of FIG. 13.

If the affected-area simulated organ 140 is held by the first holding unit 42, the second holding unit 44, the third holding unit 46, and the fourth holding unit 48 in such a preparatory orientation, the desired tension acts in the direction of the first diagonal line T1. In this state, less tension acts (in some cases, no tension acts) in the direction of the second diagonal line T2 than in the direction of the first diagonal line T1. Both the first surgical surface S1 and the third surgical surface S3 formed on the affected-area simulated organ 140 are approximately parallel to the first diagonal line T1, the reference axis C, and the second diagonal line T2. These two surfaces form a single plane in combination.

(Description of First Curved Orientation)

Suppose that the first arm 43B is swung to position the second holding unit 44 to the one-side second displacement position $P_2$ and the second arm 43C is swung to position the fourth holding unit 48 to the one-side second displacement position $Q_2$. These positions result in a first curved orientation illustrated by the solid lines in FIGS. 1 to 9. As illustrated in FIG. 2, in this second curved orientation, the second diagonal line T2 is approximately parallel to the reference axis C and skew to the first diagonal line T1, being offset to the surgical surface one side by a second distance H2. Compared to the preparatory orientation, the second holding unit 44 and the fourth holding unit 48 are drawn away from the first diagonal line T1 by the pivoting of the first arm 43B and the second arm 43C. As a result, the affected-area simulated organ 140 undergoes increased tension radial to the first diagonal line T1.

Figure 4:
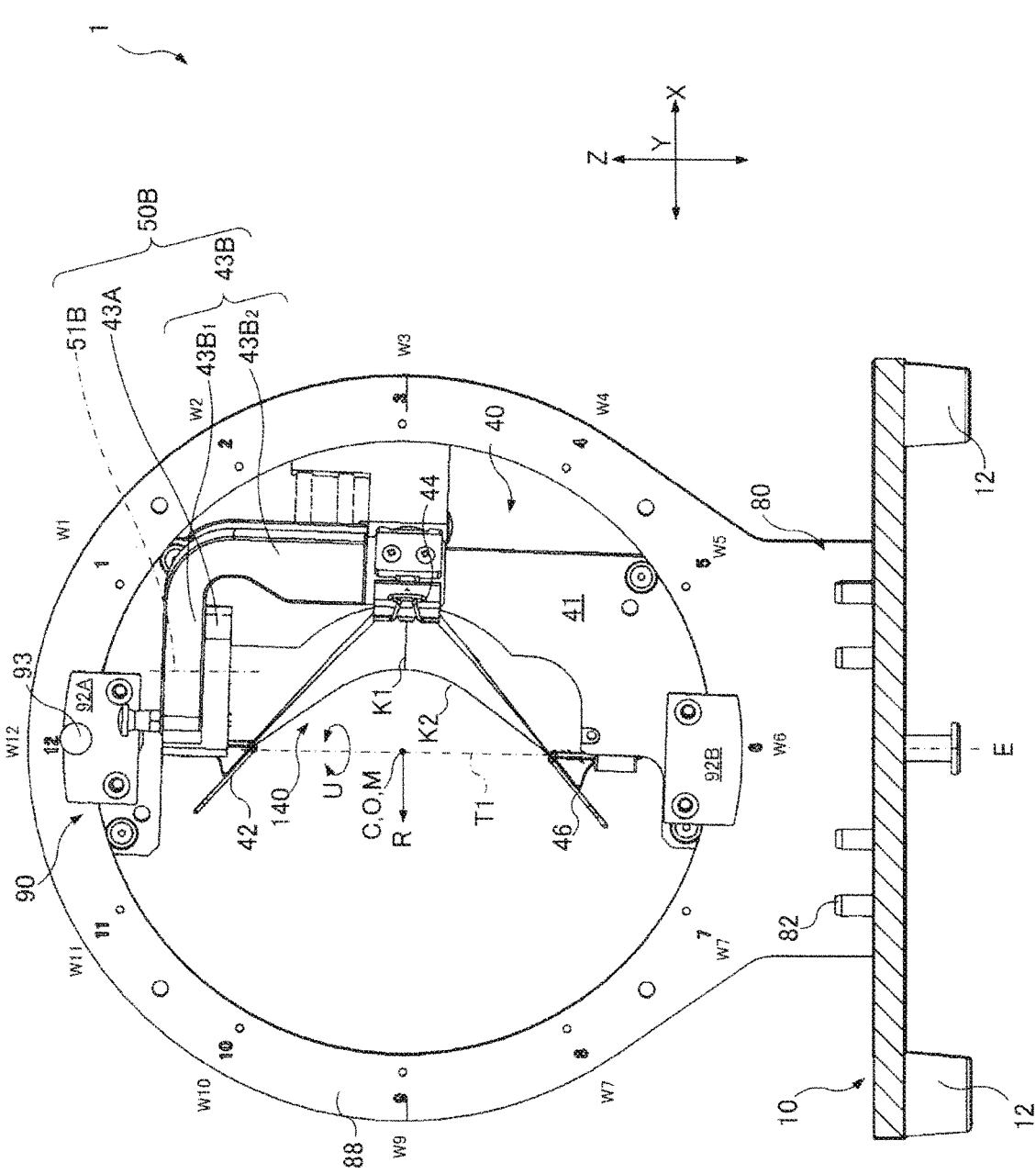
FIG. 4 is a cross-sectional view illustrating the medical device operation training apparatus in the first curved orientation, taken along line IV-IV of FIG. 3.

As illustrated in FIGS. 1 to 4, the first surgical surface S1 and the third surgical surface S3 formed on the affected-area simulated organ 140 are slopes where the amount of displacement to the surgical surface one side from the reference axis C increases with increasing distance from the first diagonal line T1 in the direction of the reference axis C. In other words, when seen along the first diagonal line T1, the vicinity of a borderline K1 between the second surgical surface S2 and the fourth surgical surface S4 forms a curved surface convex to the surgical surface counter side. Meanwhile, as illustrated in FIG. 4, when seen along the reference axis C (or the Y-axis), a borderline K2 between the first surgical surface S1 and the third surgical surface S3 forms a curved surface that is curved concave to the surgical surface one side. As a result, the combined plane of the first surgical surface S1 and the third surgical surface S3 forms a curved surface of (one-sheet) hyperboloidal shape, hyperbolic paraboloidal shape, or saddle shape in the center. Desired tension acts on this curved surface both in the axial direction of the first diagonal line T1 and in radial directions with respect to the first diagonal line T1 (from the midpoint M toward the second holding unit 44 and the fourth holding unit 48). Such a shape and state of tension are extremely similar to those of the inner wall of the distended stomach. For convenience of description, the second-path simulated organ 120 is omitted in FIG. 4.

(Description of Second Curved Orientation)

Suppose, as illustrated by dotted lines in FIG. 6, that the first arm 43B is swung to position the second holding unit 44 to the one-side first displacement position P$_1$ and the second arm 43C is swung to position the fourth holding unit 48 to the one-side first displacement position Q$_1$. This results in a second curved orientation. In this second curved orientation, the second diagonal line T2 is approximately parallel to the reference axis C and skew to the first diagonal line T1, being offset to the surgical surface one side by a first distance H1. Compared to the preparatory orientation, the second holding unit 44 and the fourth holding unit 48 are drawn away from the first diagonal line T1 by the pivoting of the first arm 43B and the second arm 43C. As a result, the affected-area simulated organ 140 undergoes increased tension radial to the first diagonal line T1.

This second curved orientation is approximately the same as the first curved orientation. However, the second diagonal line T2 is skew to the first diagonal line T1, being offset to the surgical surface one side by the first distance H1 smaller than the second distance H2. As a result, the curved surface of (one-sheet) hyperboloidal shape, hyperbolic paraboloidal shape, or saddle shape formed in the center of the combined plane of the first surgical surface S1 and the third surgical surface S3 has a higher degree of openness (greater radius of curvature) than in the second curved orientation.

(Description of Third Curved Orientation)

Suppose, as illustrated by dotted lines in FIG. 6, that the first arm 43B is swung to position the second holding unit 44 to the one-side third displacement position P$_3$ and the second arm 43C is swung to position the fourth holding unit 48 to the one-side second displacement position Q$_2$. This results in a third curved orientation.

This third curved orientation is similar to the first curved orientation, whereas the second diagonal line T2 is at an angle of a relative to the reference axis C. The second holding unit 44 in the third curved position is closer to the first diagonal line T1 than in the first curved position. This makes the radial tension caused by the second holding unit 44 smaller than that in the first curved orientation. As a result, the curved surface of (one-sheet) hyperboloidal shape, hyperbolic paraboloidal shape, or saddle shape formed in the center of the combined plane of the first surgical surface S1 and the third surgical surface S3 has a degree of openness (radius of curvature) different from those in the first and second curved orientations.

(Description of Fourth Curved Orientation)

Figure 17:
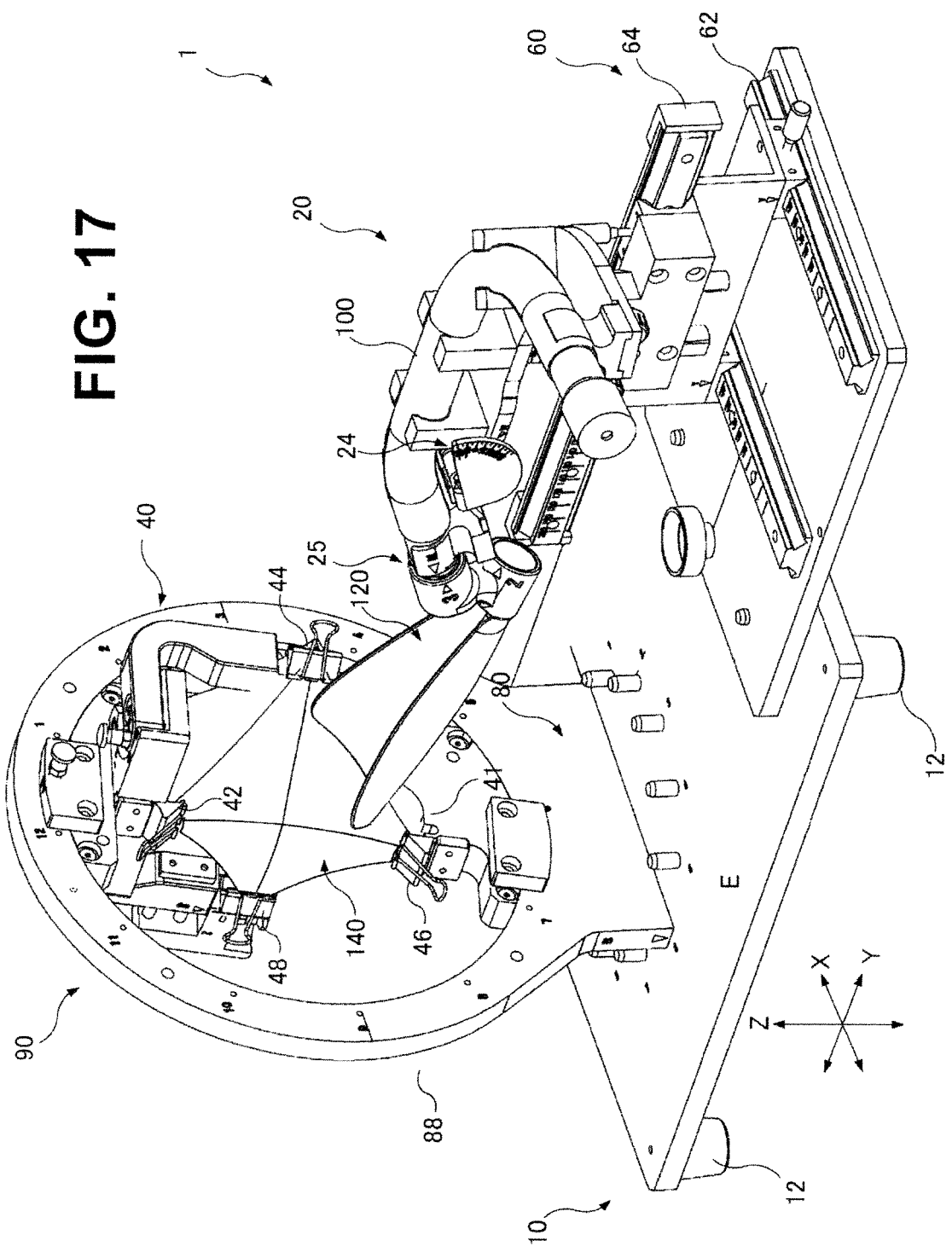
FIG. 17 is a perspective view illustrating a training setting of the medical device operation training apparatus in another orientation.

Suppose, as illustrated in FIG. 6, that the first arm 43B is swung to position the second holding unit 44 to the one-side second displacement position P$_2$ and the second arm 43C is swung to position the fourth holding unit 48 to the one-side first displacement position Q$_1$. This results in a fourth curved orientation illustrated in FIG. 17. This can direct the entirety of the first and third surgical surfaces S1 and S3 to the Y-axis operator side.

While some holding orientations have been demonstrated, the holding orientation of the affected-area simulated organ holding unit 40 can be changed in various ways depending on the combination of one freely selected from the four holding positions of the second holding unit 44 with one freely selected from the three holding positions of the fourth holding unit 48.

Suppose, for example, that the second holding unit 44 is located at the one-side third displacement position P$_3$ and the fourth holding unit 48 is located at the reference position Q$_{SET}$ This can tilt the second diagonal line T2 with respect to the reference axis C, so that the entirety of the first and third surgical surfaces S1 and S3 is directed further to the Y-axis operator side than in the fourth curved orientation. Suppose, for example, that the second holding unit 44 is located at the reference position P$_{SET}$ and the fourth holding unit 48 is located at the one-side second displacement position Q$_2$. This can tilt the second diagonal line T2 with respect to the reference axis C, so that the entirety of the first and third surgical surfaces S1 and S3 is directed to the Y-axis patient side.

(Description of Modification/Relaxed Orientation)

Figure 7:
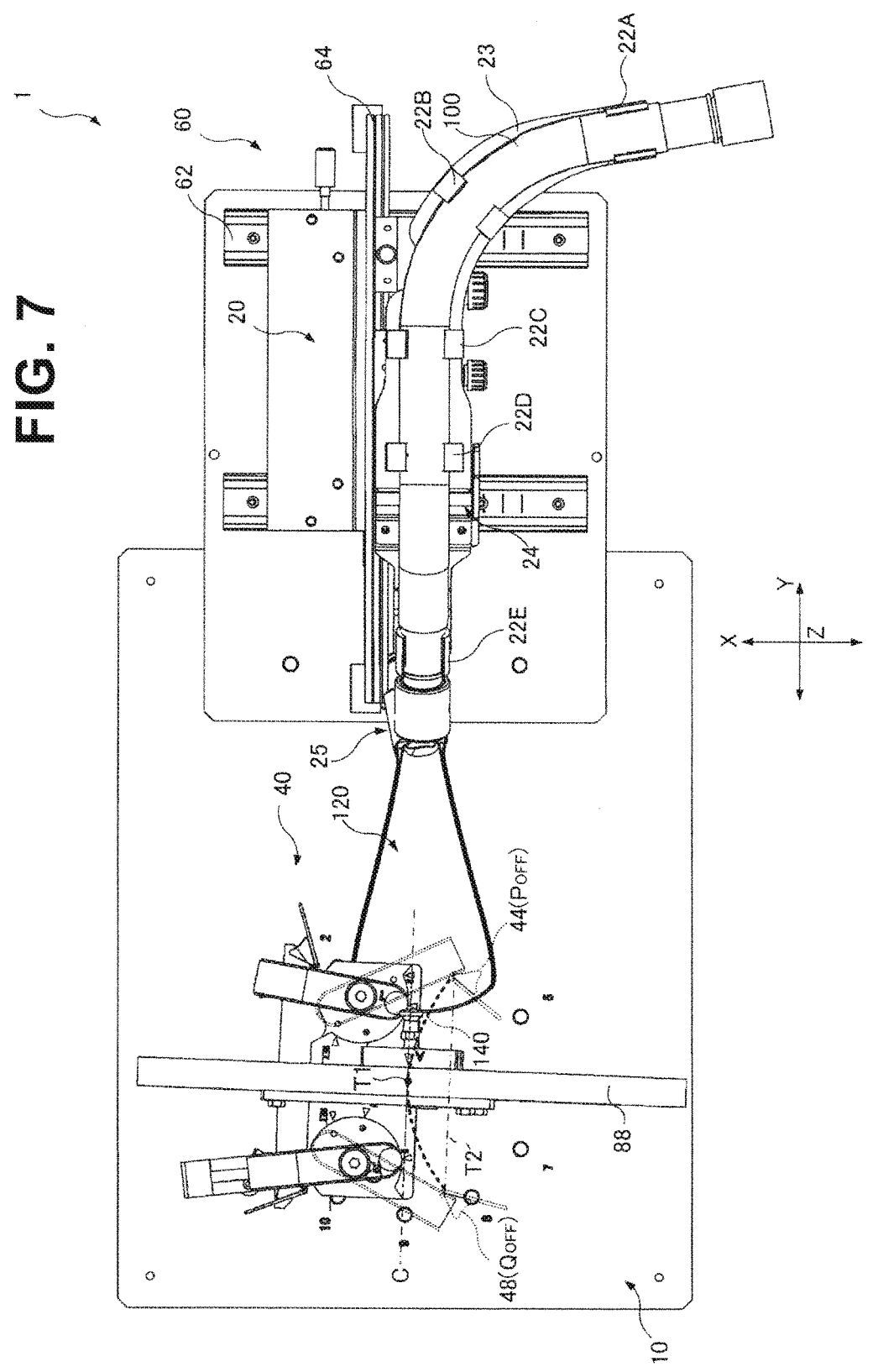
FIG. 7 is a plan view illustrating a medical device operation training apparatus as a modification.

Like a modification illustrated in FIG. 7, the second holding unit 44 may have a counter-side displacement position P$_{OFF}$ where the second holding unit 44 is displaced to the other side of the reference axis C. Similarly, the fourth holding unit 48 may have a counter-side displacement position Q$_{OFF}$ where the fourth holding unit 44 is displaced to the other side of the reference axis C. This makes the second diagonal line T2 approximately parallel to the reference axis C and skew to the first diagonal line T1, being offset to the surgical surface counter side. In addition, the second holding unit 44 and the fourth holding unit 48 are brought closer to the first diagonal line T1 by the pivoting of the first arm 43B and the second arm 43C. If the affected-area simulated organ 140 is held by the first holding unit 42, the second holding unit 44, the third holding unit 46, and the fourth holding unit 48 in such an orientation, desired tension acts in the direction of the first diagonal line T1. In this state, extremely low tension (including zero tension) acts in radial directions with respect to the first diagonal line T1. When seen along the first diagonal line T1, the first surgical surface S1 and the third surgical surface S3 form a concave slope where the amount of displacement from the reference axis C to the surgical surface counter side increases with increasing distance from the first diagonal line T1 in the direction of the reference axis C. To perform training with a surgical surface with extremely low tension, such a holding orientation can be set.

<Pedestal Planar Direction Relative Movement Mechanism>

As illustrated in FIG. 1, the pedestal planar direction relative movement mechanism 60 changes the relative positions of the first-path simulated organ 100 and the affected-area simulated organ holding unit 40 on the X-Y plane. Specifically, the pedestal planar direction relative movement mechanism 60 is an X-Y displacement table. The pedestal planar direction relative movement mechanism 60 includes:

an X-axis translation unit 62 that is disposed on the pedestal 10 and yields a relative movement of the first-path simulated organ holding unit 20 in the X-axis direction; and a Y-axis translation unit 64 that is disposed on the X-axis translation unit 62 and yields a relative movement of the first-path simulated organ holding unit 20 in the Y-axis direction. As in the setting sheet shown in FIG. 8, the X-axis translation unit 62 is set at 10 mm and 20 mm to the X-axis far side and −10 mm, −20 mm, −30 mm, −40 mm, and −50 mm to the X-axis near side with a reference point as 0. The Y-axis translation unit 64 is set within the range of 10 mm to 200 mm to the Y-axis affected area side at intervals of 10 mm with a reference point as 0.

<Pedestal Perpendicular Direction Relative Movement Mechanism>

As illustrated in FIG. 1, the pedestal perpendicular direction relative movement mechanism 70 changes the relative positions of the first-path simulated organ 100 and the affected-area simulated organ holding unit 40 in the Z-axis direction. Specifically, the pedestal perpendicular direction relative movement mechanism 70 includes a Z-axis translation unit that is disposed on the pedestal planar direction relative movement mechanism 60 and yields a relative movement of the first-path simulated organ holding unit 20 in the Z-axis direction. As in the setting sheet shown in FIG. 8, the pedestal perpendicular direction relative movement mechanism 70 is set to up to 80 mm above in the Z-axis direction at intervals of 10 mm with a reference point as 0.

<Pedestal Peri-Vertical Relative Movement Mechanism>

As illustrated in FIG. 1, the pedestal peri-perpendicular axis relative movement mechanism 80 changes the relative angle between the first-path simulated organ 100 and the affected-area simulated organ holding unit 40 about the Z-axis. Specifically, the pedestal peri-perpendicular axis relative movement mechanism 80 includes: position adjustment pins 82 that is disposed on the pedestal 10 at circumferentially regular intervals on a circumferential track about a vertical rotation axis E parallel to the Z-axis; a holding ring 88 that is disposed rotatably about the vertical rotation axis E on the pedestal 10 and holds the affected-area simulated organ holding unit 40; and a pair of position adjustment holes 84A and 84B that are formed in the bottom end of the holding ring 88 and receive a pair of position adjustment pins 82 located on a specific diameter of the circumferential track.

Here, a total of 12 position adjustment pins 82 are disposed at positions V1 to V12 at circumferential intervals of 30° about the vertical rotation axis E. As a result, the fixing angle of the holding ring 88 to the pedestal 10 about the vertical rotation axis E can be changed in 12 ways by engaging one of the position adjustment holes, 84A, with a specific position adjustment pin 82 (in FIG. 1, selected from position V6) selected from position V1 to position V12 and engaging the other position adjustment hole 84B with the opposite position adjustment pin 82 (in FIG. 1, selected from position V12) located on the same diameter as the specific position adjustment pin 82 is. This is also reflected on the setting sheet shown in FIG. 8.

<Peri-Lateral Axis Relative Movement Mechanism>

The peri-lateral axis relative movement mechanism 90 changes the relative angle between the first-path simulated organ 100 and the affected-area simulated organ holding unit 40 about a rotation axis (horizontal rotation axis/lateral axis) along the X-Y plane.

Specifically, the peri-lateral axis relative movement mechanism 90 includes: the holding ring 88 that holds the affected-area simulated organ holding unit 40; and a pair of engagement units 92A and 92B that are disposed on both ends of the first base 41 of the affected-area simulated organ holding unit 40 and engaged with the holding ring 88. The holding ring 88 has a ring shape, and is erected on the pedestal 10 with the center axis (horizontal rotation axis/lateral axis) O of the ring parallel to the X-Y plane. The affected-area simulated organ holding unit 40 is located inside the holding ring 88. The pair of engagement units 92A and 92B disposed on the first base 41 is axially and radially engaged with the holding ring 88 and circumferentially slidable. Sliding the pair of engagement units 92A and 92B along the holding ring 88 rotates the first base 41 about the center axis O of the holding ring 88. In the present embodiment, the first diagonal line T1 connecting the first holding unit 42 and the third holding unit 46 disposed on the first base 41 is roughly the same as the diameter of the holding ring 88. The midpoint M of the first diagonal line T1 crosses the center axis O of the holding ring 88.

The holding ring 88 has position adjustment holes 89 at positions W1 to W12 at circumferential intervals of 30°. One of the engagement units, 92A, includes a position adjustment pin 93 capable of engagement with the position adjustment holes 89. As a result, the fixing angle of the affected-area simulated organ 140 about the center axis O of the holding ring 88 can be changed in 12 ways by engaging the position adjustment pin 93 with a specific position adjustment hole 89 (in FIG. 1, selected from position W12) selected from position W1 to position W12. This is also reflected on the setting sheet shown in FIG. 8.

<Description of Correlation Between Training Apparatus and Organs in Human Body>

Figure 19:
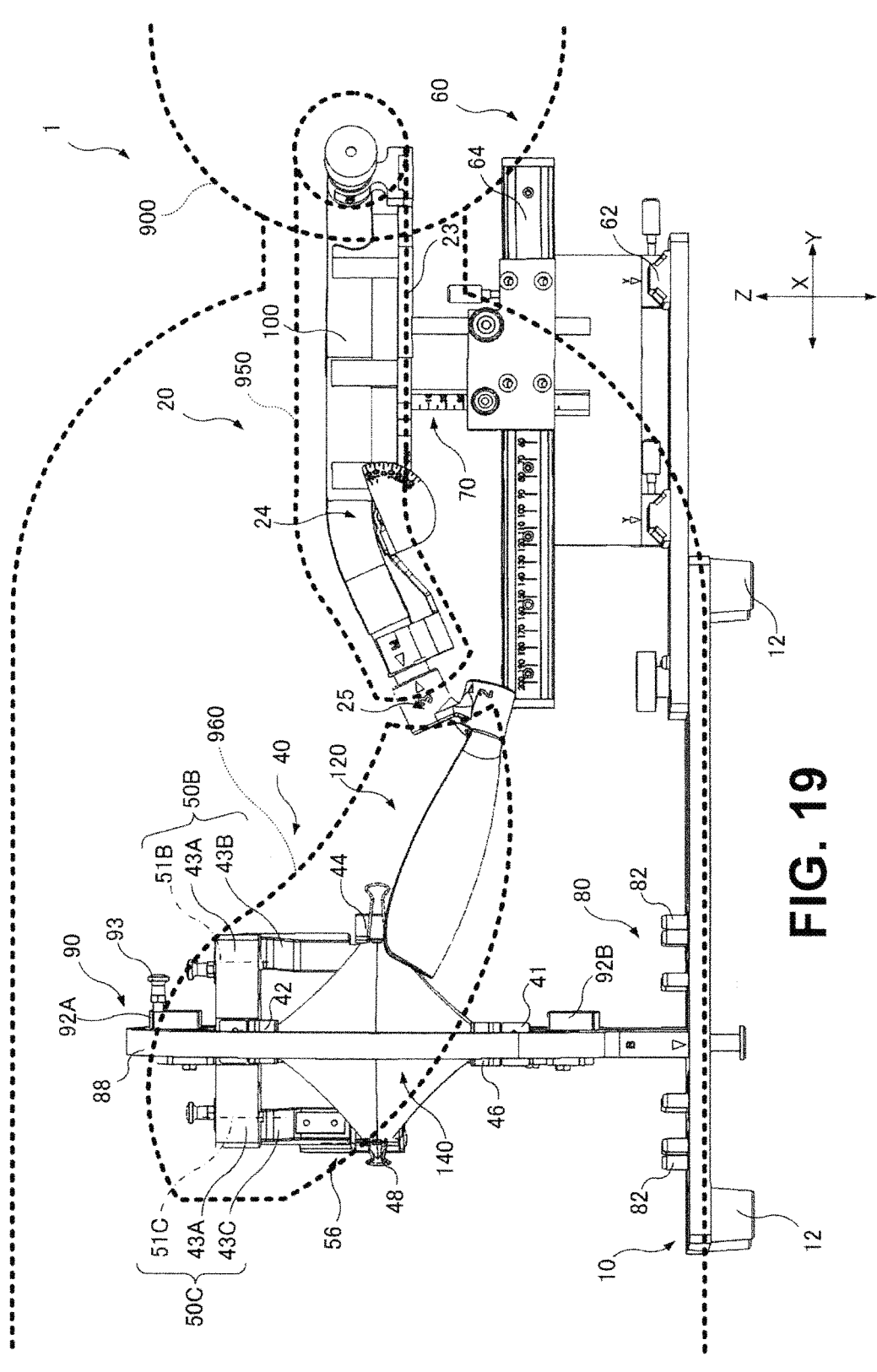
FIG. 19 is a front view illustrating a positional relationship between the medical device operation training apparatus and organs in a human body.

FIG. 19 shows a correlation between the training apparatus 1 and organs in a human body. The first-path simulated organ 100 simulates an oral cavity and esophagus 950 of a human body 900. The second-path simulated organ 120 and the affected-area simulated organ 140 simulate a part of the inner wall of a stomach 960 of the human body 900. Moreover, the relative positions of the second-path simulated organ 120 and the affected-area simulated organ 140 can be freely changed. As a result, the affected-area simulated organ 140 can simulate affected areas at various locations of the inner wall of the stomach 960.

<First Training Method of Medical Device>

Figure 9:
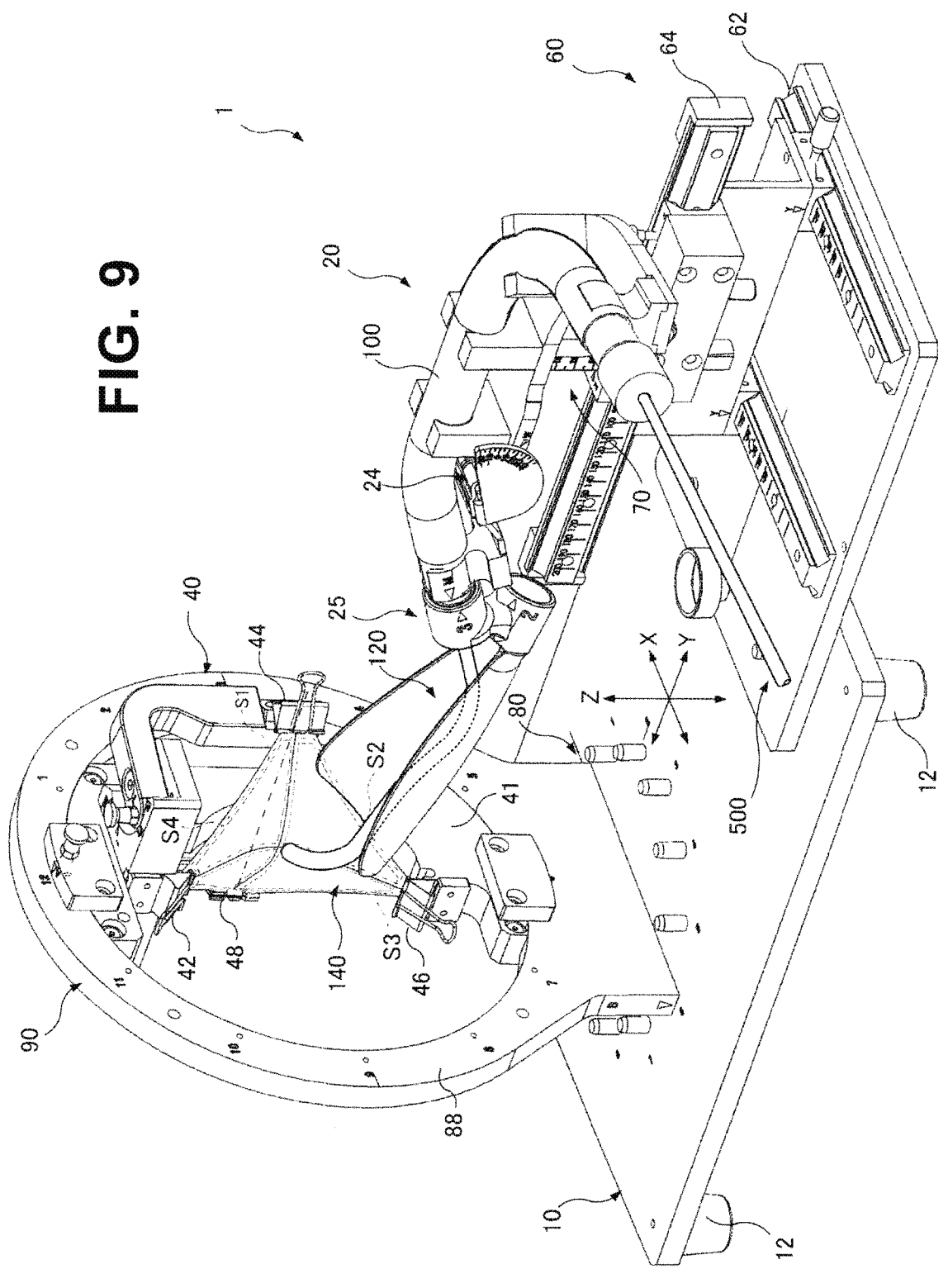
FIG. 9 is a perspective view illustrating a training setting of the medical device operation training apparatus in the first curved orientation.

FIG. 9 shows a state where training for operating an endoscope 500 is performed using the training apparatus 1. The training apparatus 1 of FIG. 9 is set so that the Y-axis translation unit 64 is at 50 mm, the X-axis translation unit 62 is at 0 mm, the pedestal perpendicular direction relative movement mechanism 70 is at 30 mm, the pedestal peri-perpendicular axis relative movement mechanism 80 is at V6, the peri-lateral axis relative movement mechanism 90 is at W12, the angle adjustment mechanism 24 is at 20°, the second holding unit 44 is at $P_2$, the fourth holding unit 48 is at $Q_2$, the tension adjustment mechanism 56 is at the far position, and the second-path simulated organ holding unit 25 is used. As a result, the surgical surface of the affected-area simulated organ 140 is directed to the X-axis near side.

The operator to be trained inserts the tip of the endoscope 500 from the upstream end of the first-path simulated organ 100. The operator pushes the endoscope 500 in, whereby the tip is protruded from the downstream end of the first-path simulated organ 100 and further guided to the downstream side of the path while being in contact with the second-path simulated organ 120. In such a state, the operator accesses the affected-area simulated organ 140 by bending the tip section of the endoscope 500 to the Y-axis far side. Here, manipulations to make good use of the reaction force that the endoscope 500 receives from the contact with the side wall on the near side of the second-path simulated organ 120 are desired. Various treatment tools, such as forceps, an injection needle, and an electronic scalpel, are then passed through the endoscope 500 and protruded from the tip of the endoscope 500 to cut into or cut out the affected-area simulated organ 140.

<Second Training Method of Medical Device>

Figure 10:
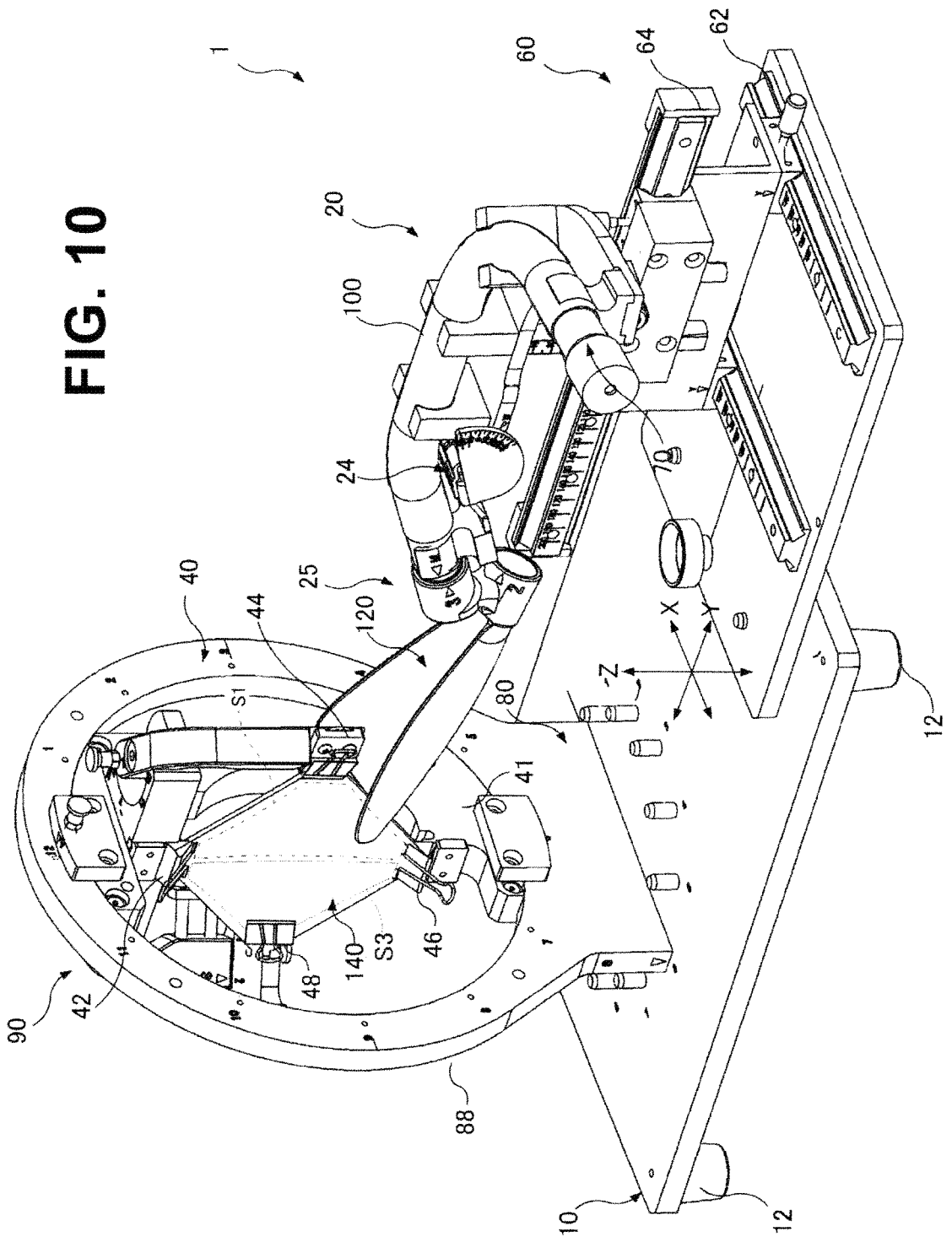
FIG. 10 is a perspective view illustrating the medical device operation training apparatus in a preparatory orientation according to a second training method.
Figure 11:
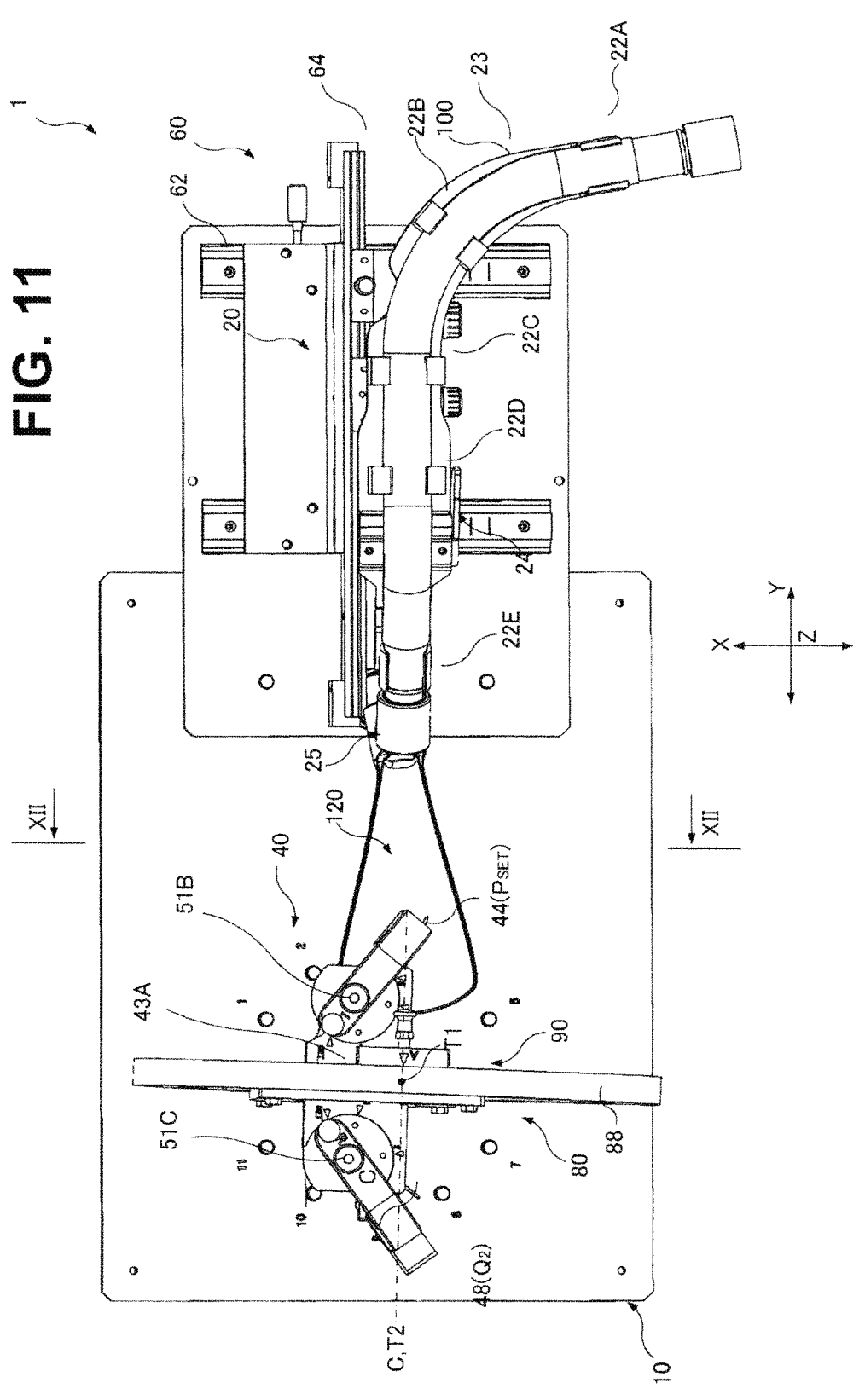
FIG. 11 is a plan view illustrating the medical device operation training apparatus in the preparatory orientation.
Figure 12:
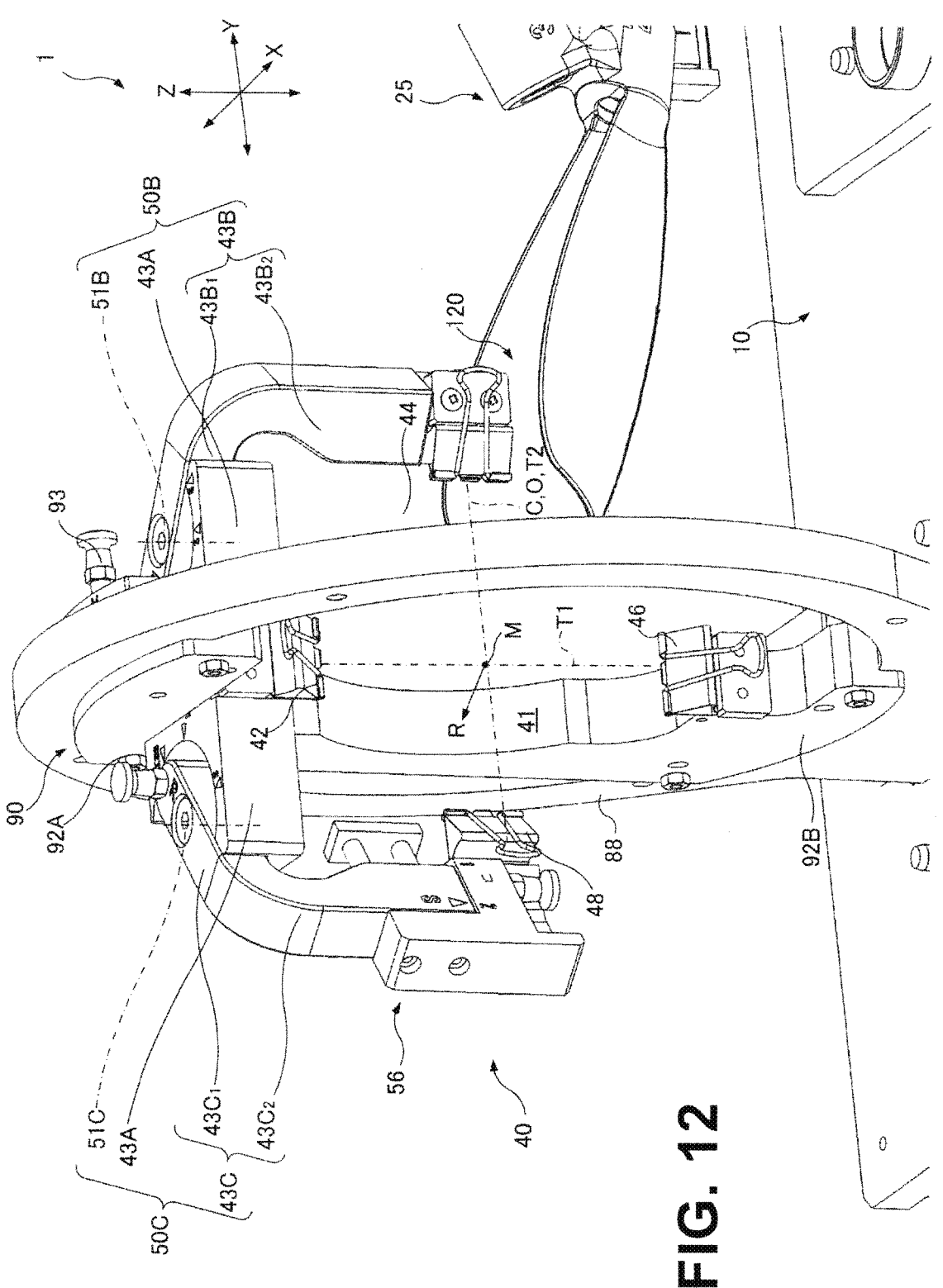
FIG. 12 is an enlarged perspective view illustrating a part of the medical device operation training apparatus in the preparatory orientation.
Figure 13:
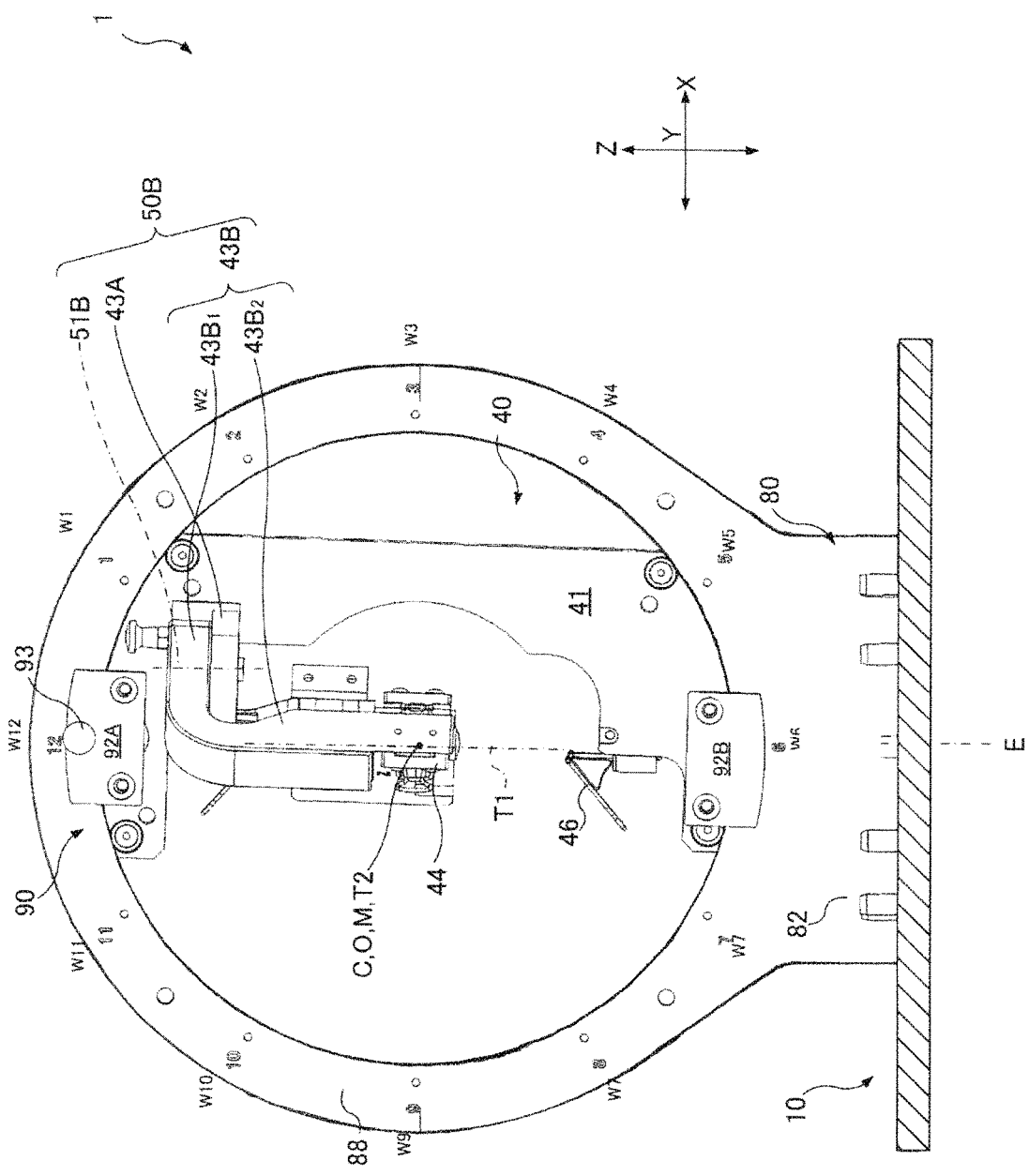
FIG. 13 is a cross-sectional view illustrating the medical device operation training apparatus in the preparatory orientation, taken along line XII-XII of FIG. 11.

FIG. 10 shows a state where training for operating the endoscope 500 is performed using the training apparatus 1. Here, FIG. 10 shows an operation for setting the affected-area simulated organ 140 on the affected-area simulated organ holding unit 40. The training apparatus 1 of FIG. 10 is set so that the Y-axis translation unit 64 is at 50 mm, the X-axis translation unit 62 is at 0 mm, the pedestal perpendicular direction relative movement mechanism 70 is at 30 mm, the pedestal peri-perpendicular axis relative movement mechanism 80 is at V6, the peri-lateral axis relative movement mechanism 90 is at W12, the angle adjustment mechanism 24 is at 20°, the second holding unit 44 is at $P_{SET}$, the fourth holding unit 48 is at $Q_{SET}$, the tension adjustment mechanism 56 is at the near position, and the second-path simulated organ holding unit 25 is used. As a result, the second holding unit 44 and the fourth holding unit 48 are located closest to the first diagonal line T1.

The operator to be trained pinches the affected-area simulated organ 140 using the first holding unit 42, the second holding unit 44, the third holding unit 46, and the fourth holding unit 48. The first arm 43B and the second arm 43C then can be pivoted into an intended orientation with an increase in tension.

<Third Training Method of Medical Device>

Figure 14:
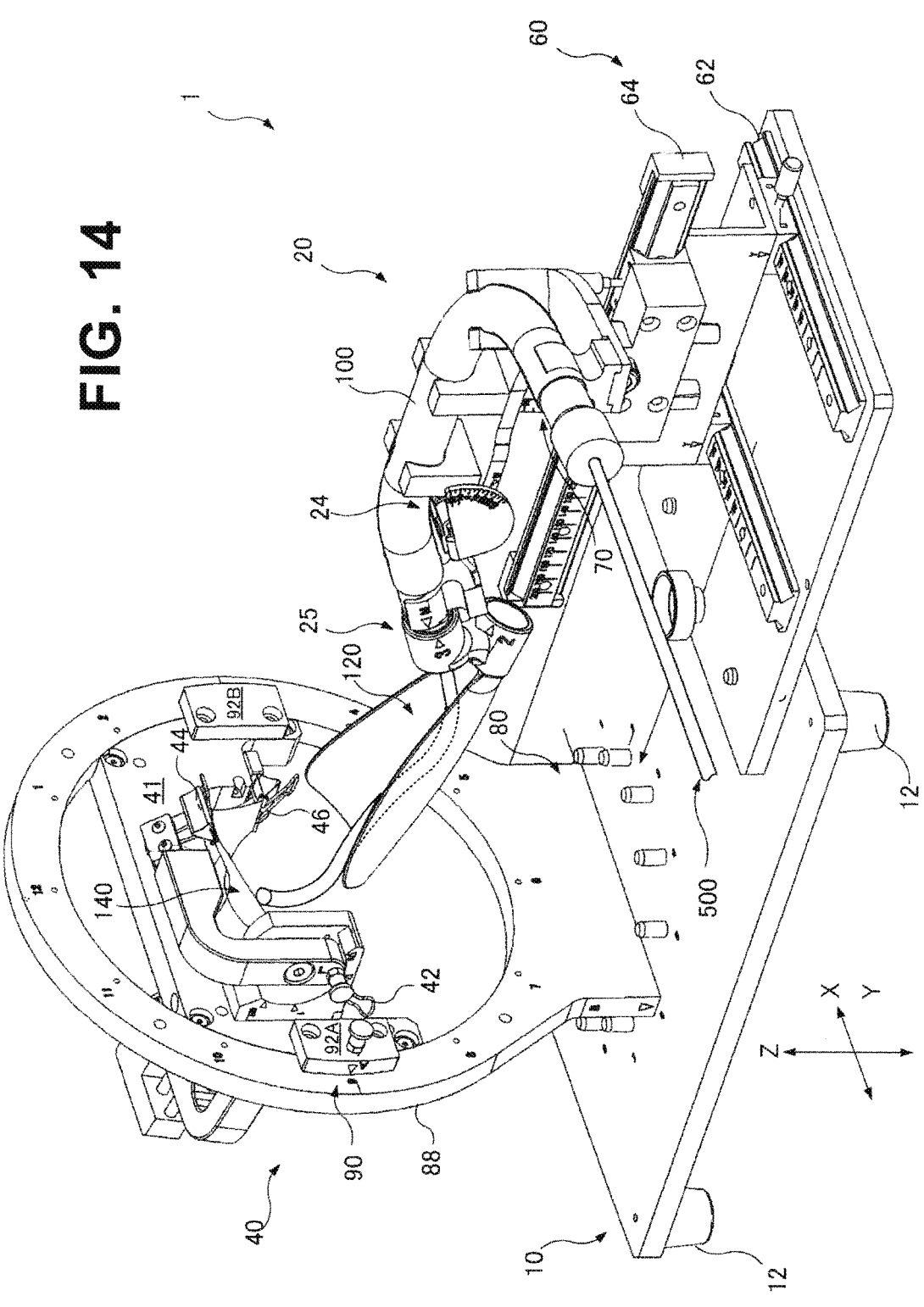
FIG. 14 is a perspective view illustrating a training setting of the medical device operation training apparatus according to a third training method.
Figure 15:
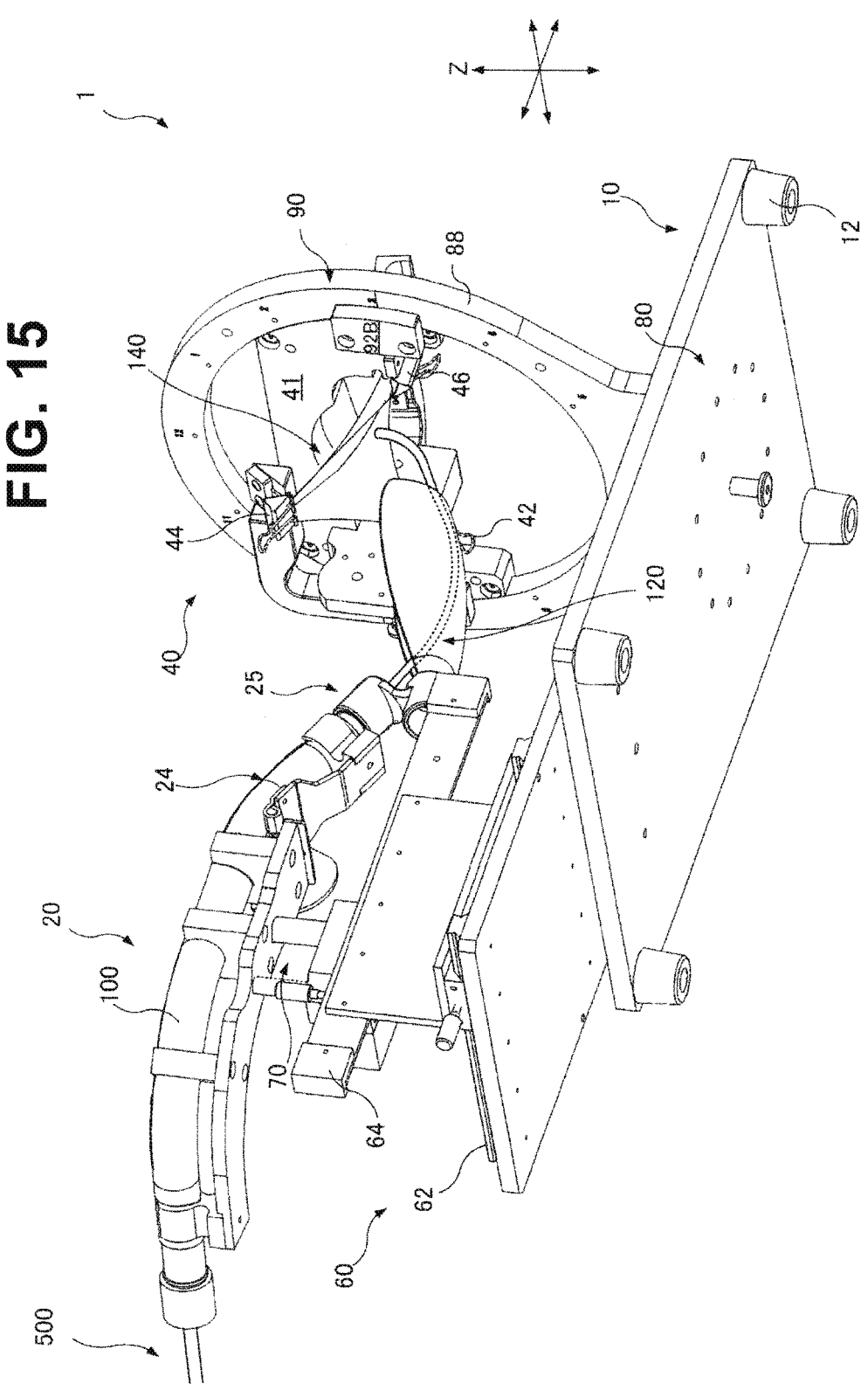
FIG. 15 is a perspective view illustrating the training setting of the medical device operation training apparatus according to the third training method, seen from behind and below.

FIGS. 14 and 15 show a state where training for operating the endoscope 500 is performed using the training apparatus 1. The training apparatus 1 of FIGS. 14 and 15 is set so that the Y-axis translation unit 64 is at 50 mm, the X-axis translation unit 62 is at 0 mm, the pedestal perpendicular direction relative movement mechanism 70 is at 30 mm, the pedestal peri-perpendicular axis relative movement mechanism 80 is at V6, the peri-lateral axis relative movement mechanism 90 is at W9, the angle adjustment mechanism 24 is at 20°, the second holding unit 44 is at $P_2$, the fourth holding unit 48 is at $Q_1$, the tension adjustment mechanism 56 is at the far position, and the second-path simulated organ holding unit 25 is used. As a result, the surgical surface of the affected-area simulated organ 140 is directed in the downward Z-axis direction.

The operator to be trained inserts the tip of the endoscope 500 from the upstream end of the first-path simulated organ 100. The operator pushes the endoscope 500 in, whereby the tip is protruded from the downstream end of the first-path simulated organ 100 and further guided to the downstream side of the path while being in contact with the second-path simulated organ 120. In such a state, the operator accesses the affected-area simulated organ 140 by bending the tip section of the endoscope 500 in the upward Z-axis direction. Here, manipulations to make good use of the reaction force that the endoscope 500 receives from the contact with the bottom of the second-path simulated organ 120 are desired. Various treatment tools, such as forceps, an injection needle, and an electronic scalpel, are passed through the endoscope 500 and protruded from the tip of the endoscope 500 to cut into or cut out the affected-area simulated organ 140.

<Fourth Training Method of Medical Device>

Figure 16:
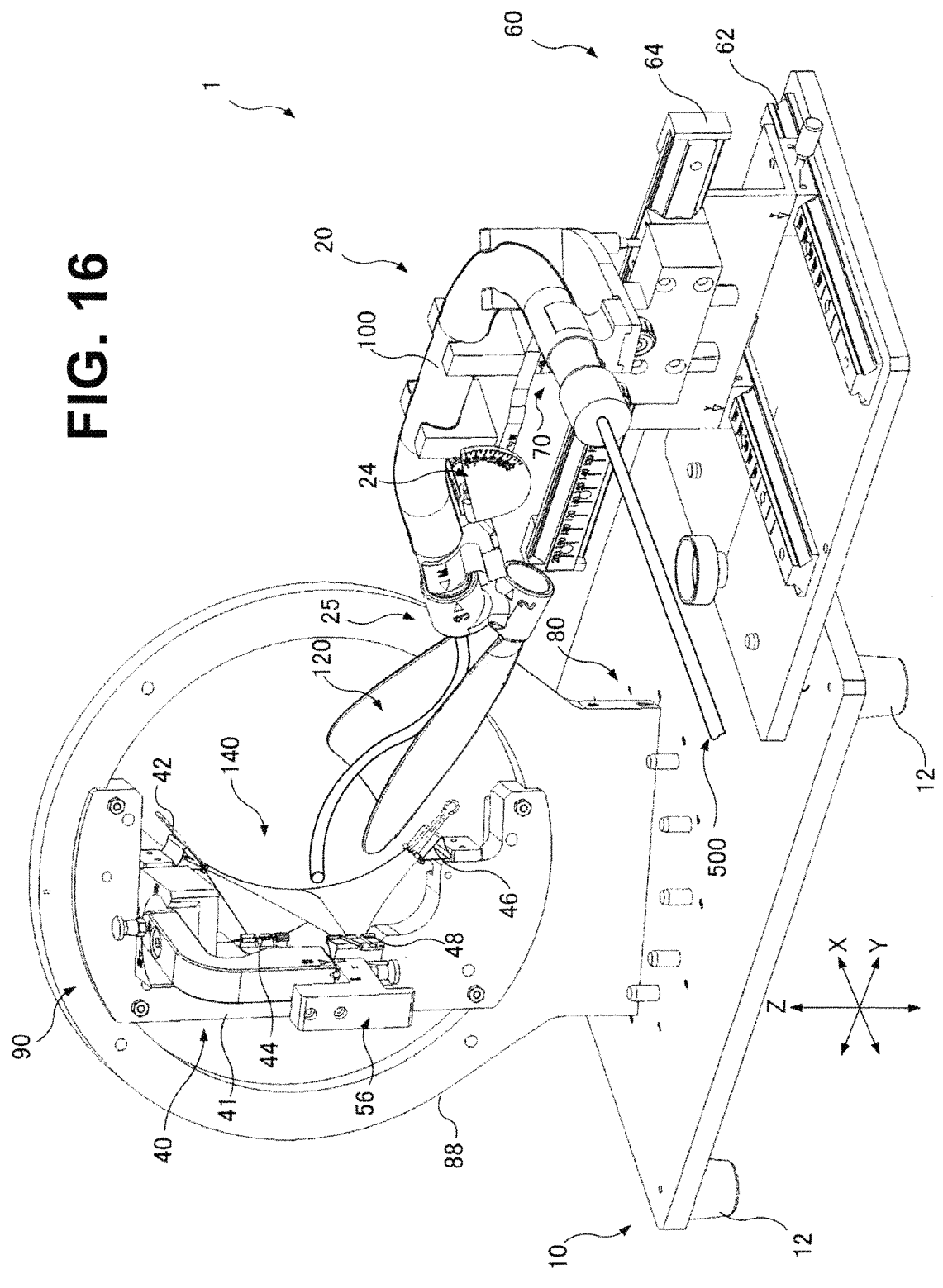
FIG. 16 is a perspective view illustrating a training setting of the medical device operation training apparatus according to a fourth training method.

FIG. 16 shows a state where training for operating the endoscope 500 is performed using the training apparatus 1. The training apparatus 1 of FIG. 16 is set so that the Y-axis translation unit 64 is at 50 mm, the X-axis translation unit 62 is at 0 mm, the pedestal perpendicular direction relative movement mechanism 70 is at 30 mm, the pedestal peri-perpendicular axis relative movement mechanism 80 is at V2, the peri-lateral axis relative movement mechanism 90 is at W12, the angle adjustment mechanism 24 is at 20°, the second holding unit 44 is at $P_2$, the fourth holding unit 48 is at $Q_1$, the tension adjustment mechanism 56 is at the far position, and the second-path simulated organ holding unit 25 is used. As a result, the surgical surface of the affected-area simulated organ 140 is directed to the Y-axis far side.

The operator to be trained inserts the tip of the endoscope 500 from the upstream end of the first-path simulated organ 100. The operator pushes the endoscope 500 in, whereby the tip is protruded from the downstream end of the first-path simulated organ 100 and further guided to the downstream side of the path while being in contact with the second-path simulated organ 120. In such a state, the operator accesses the affected-area simulated organ 140 by bending the tip section of the endoscope 500 to the Y-axis near side. Here, manipulations to make good use of the reaction force that the endoscope 500 receives from the contact with the side wall on the far side of the second-path simulated organ 120 are desired. Various treatment tools, such as forceps, an injection needle, and an electronic scalpel, are passed through the endoscope 500 and protruded from the tip of the endoscope 500 to cut into or cut out the affected-area simulated organ 140.

As described above, the training apparatus 1 according to the present embodiment can hold the sheet-like affected-area simulated organ 140 able to be incised or excised at least in part, using the affected-area simulated organ holding unit 40. Meanwhile, the first- and second-path simulated organs 100 and 120 that guide the medical device (endoscope 500) to the affected-area simulated organ 140 can be held by the first- and second-path simulated organ holding units 20 and 25. Since the affected-area simulated organ 140 and the first- and second-path simulated organ holding units 20 and 25 are independently configured, only the affected-area simulated organ 140 can be easily replaced after manipulation training.

The affected-area simulated organ 140 is a member for practicing incision and excision techniques. Since the affected-area simulated organ 140 needs to be similar to an actual living body, the manufacturing costs tend to be relatively high. As a result, the affected-area simulated organ 140 is desired to be minimized in area and volume. By contrast, sufficient operation training can be performed without making the first- and second-path simulated organ holding units 20 and 25 much similar to an actual living body. As a result, the first- and second-path simulated organ holding units 20 and 25 can be formed of materials different from that of the affected-area simulated organ 140 and used repeatedly.

Furthermore, since the affected-area simulated organ 140 has a sheet shape, the state of operation of the medical device can be visually observed from outside. In other words, an instructor other than the operator to be trained can visually observe the state of operation of the medical device from outside and give appropriate advice to the operator.

Meanwhile, since the first-path simulated organ 100 has a cylindrical structure, manipulations for inserting a medical device using a tubular organ such as the esophagus and blood vessels as the path can be practiced in a manner close to reality.

Moreover, in the present embodiment, the second-path simulated organ 100 is independently disposed downstream of the first-path simulated organ 100. The second-path simulated organ 100 can thus simulate a part of the same organ as the affected-area simulated organ 140 does. In the present embodiment, both the second-path simulated organ 100 and the affected-area simulated organ 140 simulate the inner wall of the stomach. The affected-area simulated organ 140 can simulate affected areas at various locations in the stomach by freely changing the relative positions of the two organs. This can increase training variations. Moreover, the second-path simulated organ 100 has an open-top structure, and thus has improved visibility of the state of operation of the medical device from outside.

In this training apparatus 1, the affected-area simulated organ holding unit 40 includes the tension adjustment mechanism 56 that changes the tension acting on the affected-area simulated organ 140. The affected-area simulated organ 140 of sheet shape can thus simulate the state of tension of the stomach distended by air, for example.

Moreover, in this training apparatus 1, the affected-area simulated organ holding unit 40 holds the affected-area simulated organ 140 so that a curved surface of hyperboloidal shape, hyperbolic paraboloidal shape, or saddle shape is formed at the surface of the affected-area simulated organ 140. Since a tense curved surface can be formed of the affected-area simulated organ 140 of sheet shape, the state of tension of the stomach distended by air can be simulated, for example.

As shown in FIG. 8, this training apparatus 1 includes the setting sheet that is a chart of setting values of various movable parts. Various training orientations can thus be defined in terms of the setting values in the setting sheet, and the training orientations can be easily reproduced. This enables management of the progress of manipulation training.

It will be understood that the present invention is not limited to the aforementioned embodiment, and various changes can be made without departing from the gist of the present invention.

The invention claimed is:

1. A medical device operation training apparatus used in performing training for operation of a medical device, the medical device operation training apparatus comprising:

an affected-area simulated organ holding unit configured to hold a sheet of an affected-area simulated organ able to be incised or excised at least in part; and a path simulated organ holding unit configured to hold a path simulated organ for guiding the medical device to the sheet of the affected-area simulated organ;

wherein the affected-area simulated organ holding unit includes at least a first holding unit, a second holding unit, a third holding unit, and a fourth holding unit each configured to hold the sheet of the affected-area simulated organ;

wherein the first holding unit, the second holding unit, and the third holding unit are disposed in an orientation to form vertices of a triangle, whereby a surgical surface formed within the triangle is formed at a surface of the sheet of the affected-area simulated organ;

wherein the first holding unit, the second holding unit, the third holding unit, and the fourth holding unit are disposed to surround the sheet of the affected-area simulated organ in an order around the sheet of the first holding unit, the second holding unit, the third holding unit, and the fourth holding unit;

wherein a first diagonal line between the first holding unit and the third holding unit and a second diagonal line between the second holding unit and the fourth holding unit are positioned to an orientation of skew lines; and wherein a shape of the surgical surface is adjustable by changing a distance between the first diagonal line and the second diagonal line.

2. The medical device operation training apparatus according to claim 1, wherein the affected-area simulated organ holding unit includes a tension adjustment mechanism configured to change tension acting on the sheet of the affected-area simulated organ.

3. The medical device operation training apparatus according to claim 1, wherein the affected-area simulated organ holding unit includes a second holding unit displacement mechanism configured to displace the second holding unit in a direction including at least a rotational direction component about a line connecting the first holding unit and the third holding unit.

4. The medical device operation training apparatus according to claim 1, wherein the affected-area simulated organ holding unit holds the sheet of the affected-area simulated organ so that a surface of the sheet of the affected-area simulated organ forms a curved surface of hyperboloidal shape, hyperbolic paraboloidal shape, or saddle shape.

5. The medical device operation training apparatus according to claim 1, wherein the affected-area simulated organ holding unit holds the sheet of the affected-area simulated organ so that the surface of the sheet of the affected-area simulated organ forms a curved surface of hyperboloidal shape, hyperbolic paraboloidal shape, or saddle shape.

6. A medical device operation training apparatus used in performing training for operation of a medical device, the medical device operation training apparatus comprising:

an affected-area simulated organ holding unit configured to hold a sheet of an affected-area simulated organ able to be incised or excised at least in part;

a path simulated organ holding unit configured to hold a path simulated organ for guiding the medical device to the sheet of the affected-area simulated organ;

a peri-lateral axis relative movement mechanism configured to change a relative angle between the path simulated organ and the sheet of the affected-area simulated organ about a lateral axis extending in a horizontal direction; and a pedestal peri-perpendicular axis relative movement mechanism configured to change a relative angle between the path simulated organ and the sheet of the affected-area simulated organ about a vertical axis extending in a vertical direction.

7. A medical device operation training apparatus used in performing training for operation of a medical device, the medical device operation training apparatus comprising:

an affected-area simulated organ holding unit configured to hold an affected-area simulated organ that is formed of a sheet material able to be incised or excised at least in part and that simulates a part of an inner wall of a stomach;

a first path simulated organ holding unit configured to hold, along a predetermined path, a tubular first path simulated organ for guiding the medical device to the affected-area simulated organ; and a second path simulated organ holding unit configured to hold a second path simulated organ that is provided between the affected-area simulated organ and the tubular first path simulated organ and that simulates another part of the inner wall of the stomach;

wherein the affected-area simulated organ holding unit includes at least a first holding unit, a second holding unit, and a third holding unit each configured to sand-
wich and hold the affected-area simulated organ; and
wherein the first holding unit, the second holding unit, and
the third holding unit are disposed in an orientation to
form vertices of a triangle, whereby a surgical surface
is formed, in the affected-area simulated organ,
between portions sandwiched by the first holding unit,
the second holding unit, and the third holding unit.

8. The medical device operation training apparatus
according to claim 7, wherein the second path simulated
organ is open-topped.

9. The medical device operation training apparatus
according to claim 7, wherein the second path simulated
organ and the affected-area simulated organ move relative to
each other.

10. The medical device operation training apparatus
according to claim 7, wherein the second path simulated
organ has a maximum width greater than a width of an inner
wall of the tubular first path simulated organ.

11. The medical device operation training apparatus
according to claim 7, further comprising a peri-lateral axis
relative movement mechanism configured to change a rela-
tive position of the affected-area simulated organ holding
unit with respect to the first path simulated organ holding
unit by rotating the affected-area simulated organ holding
unit about a lateral axis extending in a horizontal direction
relative to the first path simulated organ holding unit.

\* \* \* \* \*